(12) United States Patent
Jaehne et al.

(10) Patent No.: US 7,407,938 B2
(45) Date of Patent: Aug. 5, 2008

(54) RING-SUBSTITUTED DIPHENYLAZETIDINONES, PROCESS FOR THEIR PREPARATION, MEDICAMENTS COMPRISING THESE COMPOUNDS, AND THEIR USE

(75) Inventors: Gerhard Jaehne, Frankfurt (DE); Wendelin Frick, Hünstetten-Beuerbach (DE); Stefanie Flohr, Basel (CH); Andreas Lindenschmidt, Bad Soden (DE); Heiner Glombik, Hofheim (DE); Werner Kramer, Mainz-Laubenheim (DE); Hubert Heuer, Schwabenheim (DE); Hans-Ludwig Schaefer, Hochheim (DE)

(73) Assignee: Sanofi-Aventis Deutschland GmbH (DE)

( * ) Notice: Subject to any disclaimer, the term of this patent is extended or adjusted under 35 U.S.C. 154(b) by 0 days.

(21) Appl. No.: 11/544,746

(22) Filed: Oct. 10, 2006

(65) Prior Publication Data
US 2007/0037787 A1    Feb. 15, 2007

Related U.S. Application Data

(62) Division of application No. 10/463,807, filed on Jun. 18, 2003, now Pat. No. 7,176,194.

(60) Provisional application No. 60/411,984, filed on Sep. 19, 2002.

(30) Foreign Application Priority Data
Jun. 19, 2002    (DE) ............................ 102 27 506

(51) Int. Cl.
*C07D 205/08* (2006.01)
*C07K 2/00* (2006.01)
*A61K 38/08* (2006.01)
*A61K 31/05* (2006.01)
*A61K 31/06* (2006.01)
*A61K 31/07* (2006.01)
*A61K 31/397* (2006.01)
*A61P 9/10* (2006.01)
*A61P 3/06* (2006.01)

(52) U.S. Cl. ........................... 514/15; 540/200; 514/16; 514/17; 514/18; 514/19; 514/210.02; 930/280

(58) Field of Classification Search ............ 514/210.02; 540/200
See application file for complete search history.

(56) References Cited

U.S. PATENT DOCUMENTS

| | | | |
|---|---|---|---|
| 5,656,624 | A | 8/1997 | Vaccaro et al. |
| 5,756,470 | A | 5/1998 | Yumibe et al. |
| 5,889,002 | A | 3/1999 | Nielsen et al. |
| 6,225,310 | B1 | 5/2001 | Nielsen et al. |
| 6,268,343 | B1 | 7/2001 | Knudsen et al. |
| 6,498,156 | B2 | 12/2002 | Glombik et al. |
| 6,632,456 | B1* | 10/2003 | Backstrom et al. .......... 424/489 |
| 6,703,386 | B2 | 3/2004 | Glombik et al. |
| 2002/0039774 | A1 | 4/2002 | Kramer et al. |

(Continued)

FOREIGN PATENT DOCUMENTS

| | | |
|---|---|---|
| DE | 100 64 398 A1 | 6/2002 |
| DE | 101 52 981 A1 | 5/2003 |
| WO | WO 96/19450 | 6/1996 |
| WO | WO 97/16455 | 5/1997 |
| WO | WO 97/26265 | 7/1997 |
| WO | WO 97/41097 | 11/1997 |
| WO | WO 97/45406 | 12/1997 |
| WO | WO 98/08871 | 3/1998 |
| WO | WO 99/03861 | 1/1999 |
| WO | WO 00/63703 | 10/2000 |
| WO | WO 02/18432 A2 | 3/2002 |
| WO | WO 02/50027 | 6/2002 |
| WO | WO 02/50060 | 6/2002 |
| WO | WO 02/50068 | 6/2002 |
| WO | WO 2004/005247 A1 | 1/2004 |

OTHER PUBLICATIONS

Murthy et al., Biochem. J. (2004) 377 (545-552).*
Robl et al., J. Med. Chem. 44(6):851-856 (2001) (Abstract only).*
Badiu, Endocr Pract. Jan.-Feb. 1999;5(1):10-6 (abstract only).*
Moran et al., J Biol Chem, vol. 273, Issue 20, 12259-12266, May 15, 1998.*
Shirai, Infect Immun. Nov. 1990;58(11):3568-73.*
ChemID Plus Advanced Full record for NMI 8739 (2004).*
Kaska, J., M.S. Thesis, Worcester Polytechnic Institute, (2003), including abstract.*

(Continued)

*Primary Examiner*—Mark L Berch
(74) *Attorney, Agent, or Firm*—Finnegan, Henderson, Farabow, Garret, & Dunner LLP.

(57) ABSTRACT

One embodiment of the invention relates to compounds of the formula I,

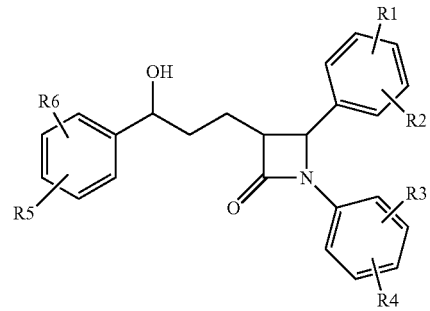

in which R1, R2, R3, R4, R5 and R6 have the meanings given in the specification. Other embodiments of the invention relate to physiologically acceptable salts of compounds of formula I, to processes for their preparation and to medicaments comprising these compounds. The compounds of the invention are suitable for use, for example, as hypolipidemics.

15 Claims, No Drawings

U.S. PATENT DOCUMENTS

| | | |
|---|---|---|
| 2002/0128252 A1 | 9/2002 | Glombik et al. |
| 2002/0128253 A1 | 9/2002 | Glombik et al. |
| 2002/0137689 A1 | 9/2002 | Glombik et al. |
| 2004/0067913 A1 | 4/2004 | Jaehne et al. |
| 2004/0077623 A1 | 4/2004 | Jaehne et al. |
| 2004/0082561 A1 | 4/2004 | Jaehne et al. |
| 2007/0135357 A1* | 6/2007 | Sings et al. .................. 514/25 |
| 2007/0142304 A1* | 6/2007 | Alenfalk et al. ............... 514/19 |

OTHER PUBLICATIONS esp@cenet abstract of DE 101 52 981, May 8, 2003.

esp@cenet abstract of DE 100 64 398, Jun. 27, 2002.

International Search Report, PCT/EP 03/05816, dated Aug. 28, 2003.

R.M. Castaner et al., "Hypolipidemic Cholesterol Absorption Inhibitor", Drugs of the Future 2000, 25(7), pp. 679-685, (2000).

A.R. Hilgers, et al., "Caco-2 Cell Monolayers as a Model for Drug Transport Across the Intestinal Mucosa", Pharmaceutical Research, vol. 7, No. 9, pp. 902-910, (1990).

L. Schröder, "The Peptides", vol. 1, New York 1965, pp. XXII-XXIII, (2000).

Houben-Weyl, Wünsch, "10. Einteilung und Nomenklatur der Peptide und ihrer Derivate," in Methoden de Organischen Chemie, Stuttgart, Germany, Band XV, Seiten 1 und 2, pp. 1-12, (1974).

Vaccaro, Wayne D., et al., "Sugar-Substituted 2-Azetidinones As Cholesterol Absorption Inhibitors," Bioorganic & Medicinal Chemistry Letters 8(1998):35-40.

Vaccaro, Wayne D., et al., "Sugar-Substituted 2-Azetidinone Cholesterol Absorption Inhibitors: Enhanced Potency by Modification of the Sugar," Bioorganic & Medicinal Chemistry Letters 8(1998):313-318.

van Heek, Margaret et al., "Comparison of the activity and disposition of the novel cholesterol absorption inhibitor, SCH58235, and Its glucuronlde, SCH60663," British Journal of Pharmacology 129:1748-1754 (2000).

Zaks, Aleksey, et al., "Enzymatic Glucuronidation of a Novel Cholesterol Absorption Inhibitor, SCH 58235," Applied Biochemistry and Biotechnology, 73:205-213 (1998).

* cited by examiner

RING-SUBSTITUTED DIPHENYLAZETIDINONES, PROCESS FOR THEIR PREPARATION, MEDICAMENTS COMPRISING THESE COMPOUNDS, AND THEIR USE

This application is a Divisional of application Ser. No. 10/463,807, filed on Jun. 18, 2003 now U.S. Pat. No. 7,176,194, which claims the benefit of the filing dates of German Patent Application Number 10227506.8, filed on Jun. 19, 2002, and U.S. Provisional Application Number 60/411,984, filed Sep. 19, 2002. All three applications are hereby incorporated by reference.

One embodiment of the invention relates to ring-substituted diphenylazetidinones, their physiologically acceptable salts and derivatives having physiological functions.

Diphenylazetidinones (such as, for example, ezetimibe) and their use for treating hyperlipidemia, arteriosclerosis and hypercholesterolemia have already been described [cf. Drugs of the Future 2000, 25(7):679-685 and U.S. Pat. No. 5,756,470].

One embodiment of the invention provides further compounds having a therapeutically utilizable hypolipidemic action. For example, one embodiment of the invention relates to novel compounds which, compared to the compounds described in the prior art, are absorbed to a very low extent. Very low absorption is to be understood as meaning an intestinal absorption of less than about 10%, preferably less than or equal to about 5%.

In one embodiment, absorption of the novel compounds may be less than that of ezetimibe.

In general, pharmaceutically active compounds that are absorbed to a low extent may have considerably fewer side-effects.

Accordingly, on emebodiment of the invention relates to compounds of the formula I

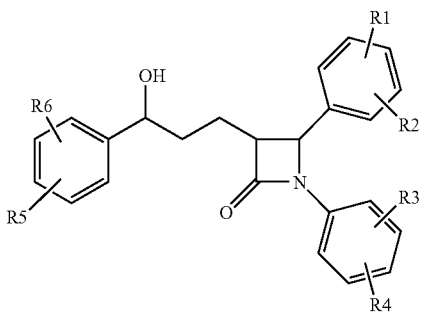

wherein
R1, R2, R3, R4, R5, and R6, independently of one another, are chosen from:
$(C_1-C_{30})$-alkylene-$(LAG)_q$,
  wherein at least one carbon atom of the alkylene radical is replaced by aryl or heteroaryl radicals, which are unsubstituted or substituted one, two, or three times by R7; or by $(C_3-C_{10})$-cycloalkyl or heterocycloalkyl radicals, which are unsubstituted or substituted one, two, three, or four times by R7,
  and wherein at least one-carbon atom of the alkylene radical is optionally replaced by a radical chosen from: —S(O)$_m$— (wherein m=0-2), —O—, —(C=O)—, —(C=S)—, —CH=CH—, —C≡C—, —N(($C_1-C_6$)-alkyl)-, —N(phenyl), —N(($C_1-C_6$)-alkyl-phenyl)-, —N(CO—(CH$_2$)$_{1-10}$—COOH)— and —NH—;

H, F, Cl, Br, I, CF$_3$, NO$_2$, N$_3$, CN, COOH, COO($C_1-C_6$)-alkyl, CONH$_2$, CONH($C_1-C_6$)-alkyl, CON[($C_1-C_6$)-alkyl]$_2$, ($C_1-C_6$)-alkyl, ($C_2-C_6$)-alkenyl, ($C_2-C_6$)-alkynyl, or O—($C_1-C_6$)-alkyl, wherein the alkyl radical is unsubstituted or at least one hydrogen in the alkyl radical is replaced by fluorine;

SO$_2$—NH$_2$, SO$_2$NH($C_1-C_6$)-alkyl, SO$_2$N[($C_1-C_6$)-alkyl]$_2$, S—($C_1-C_6$)-alkyl, S—(CH$_2$)$_n$-phenyl, SO—($C_1-C_6$)-alkyl, SO—(CH$_2$)$_n$-phenyl, SO$_2$-($C_1-C_6$)-alkyl, or SO$_2$—(CH$_2$)$_n$-phenyl, wherein n=0-6, and wherein the phenyl radical is unsubstituted or substituted one or two times, each substituent chosen independently from: F, Cl, Br, OH, CF$_3$, NO$_2$, CN, OCF$_3$, O—($C_1-C_6$)-alkyl, ($C_1-C_6$)-alkyl, or NH$_2$;

NH$_2$, NH—($C_1-C_6$)-alkyl, N(($C_1-C_6$)-alkyl)$_2$, NH($C_1-C_7$)-acyl, phenyl, or O—(CH$_2$)$_n$-phenyl, wherein n=0-6, wherein the phenyl ring is unsubstituted or substituted one, two, or three times, each substituent chosen independently from: F, Cl, Br, I, OH, CF$_3$, NO$_2$, CN, OCF$_3$, O—($C_1-C_6$)-alkyl, ($C_1-C_6$)-alkyl, NH$_2$, NH($C_1-C_6$)-alkyl, N(($C_1-C_6$)-alkyl)$_2$, SO$_2$—CH$_3$, COOH, COO—($C_1-C_6$)-alkyl, or CONH$_2$;

R7 is F, Cl, Br, I, CF$_3$, NO$_2$, N$_3$, CN, COOH, COO($C_1-C_6$)-alkyl, CONH$_2$, CONH($C_1-C_6$)-alkyl, CON[($C_1-C_6$)-alkyl]$_2$, ($C_1-C_6$)-alkyl, ($C_2-C_6$)-alkenyl, ($C_2-C_6$)-alkynyl, or O—($C_1-C_6$)-alkyl, wherein the alkyl radical is unsubstituted or at least one hydrogen in the alkyl radical is replaced by fluorine;

PO$_3$H$_2$, SO$_3$H, SO$_2$—NH$_2$, SO$_2$NH($C_1-C_6$)-alkyl, SO$_2$N[($C_1-C_6$)-alkyl]$_2$, S—($C_1-C_6$)-alkyl, S—(CH$_2$)$_n$-phenyl, SO—($C_1-C_6$)-alkyl, SO—(CH$_2$)$_n$-phenyl, SO$_2$-($C_1-C_6$)-alkyl, or SO$_2$—(CH$_2$)$_n$-phenyl, wherein n=0-6, and wherein the phenyl radical is unsubstituted or substituted one or two times, each substituent chosen independently from: F, Cl, Br, OH, CF$_3$, NO$_2$, CN, OCF$_3$, O—($C_1-C_6$)-alkyl, ($C_1-C_6$)-alkyl, or NH$_2$; or C(NH)(NH$_2$), NH$_2$, NH—($C_1-C_6$)-alkyl, N(($C_1-C_6$)-alkyl)$_2$, NH($C_1-C_7$)-acyl, phenyl, or O—(CH$_2$)$_n$-phenyl, wherein n=0-6, and wherein the phenyl ring is unsubstituted or substituted one, two, or three times, each substituent chosen independently from: F, Cl, Br, I, OH, CF$_3$, NO$_2$, CN, OCF$_3$, O—($C_1-C_6$)-alkyl, ($C_1-C_6$)-alkyl, NH$_2$, NH($C_1-C_6$)-alkyl, N(($C_1-C_6$)-alkyl)$_2$, SO$_2$—CH$_3$, COOH, COO—($C_1-C_6$)-alkyl, or CONH$_2$;

wherein (LAG) is:
  a sugar residue, disugar residue, trisugar residue, tetrasugar residue; a sugar acid, an amino sugar;
  an amino acid residue, an oligopeptide residue comprising 2 to 9 amino acids; or
  an acyclic, mono-, di- or tricyclic trialkylammonium radical, an acyclic mono-, di- or tricyclic trialkylammoniumalkyl radical, —O—(SO$_2$)—OH; —(CH$_2$)$_{0-10}$—SO$_3$H; —(CH$_2$)$_{0-10}$—P(O)(OH)$_2$, —(CH$_2$)$_{0-10}$—O—P(O)(OH)$_2$, —(CH$_2$)$_{0-10}$—COOH, —(CH$_2$)$_{0-10}$-C(=NH)(NH$_2$); —(CH$_2$)$_{0-10}$—C(=NH)(NHOH); or —NR8-C(=NR9)(NR10R11);

wherein q=1-5 and wherein R8, R9, R10 and R11, independently of one another are chosen from H, ($C_1-C_6$)-alkyl, phenyl, ($C_1-C_6$)-alkyl-phenyl, or ($C_3-C_8$)-cycloalkyl), and wherein at least one of the radicals R1 to R6 must have the meaning:

($C_1$-$C_{30}$)-alkylene-(LAG)$_q$, wherein at least one carbon atom of the alkylene radical is replaced by: aryl or heteroaryl radicals, which are a unsubstituted or substituted one, two, or three times by R7; or by ($C_3$-$C_{10}$)-cycloalkyl or heterocycloalkyl radicals, which are unsubstituted or substituted one, two, three, or four times by R7; and wherein at least one carbon atom of the alkylene radical is optionally replaced by a radical chosen from: —S(O)$_m$— (wherein m=0-2), —O—, —(C=O)—, —(C=S)—, —CH=CH—, —C≡C—, —N(($C_1$-$C_6$)-alkyl)-, —N(phenyl)-, —N(($C_1$-$C_6$)-alkyl-phenyl)-, —N(CO—(CH$_2$)$_{1-10}$—COOH)— and —NH—;

or a physiologically acceptable salt thereof, in any stereoisomeric form, or a mixture of any such compounds in any ratio.

In one embodiment of the invention, at least one of the radicals R1 to R6 in the compounds of the formula I has the meaning ($C_1$-$C_{30}$)-alkylene-(LAG)$_q$, wherein q=1-5 and wherein at least one carbon atom of the alkylene radical is replaced by: aryl or heteroaryl radicals, which are unsubstituted or substituted one, two, or three times by R7; or by ($C_3$-$C_{10}$)-cycloalkyl or heterocycloalkyl radicals, which are unsubstituted or substituted one, two, three, or four times by R7, and wherein at least one carbon atom of the alkylene radical is optionally replaced by a radical chosen from: —S(O)$_m$— (wherein m=0-2), —O—, —(C=O)—, —(C=S)—, —CH=CH—, —C≡C—, —N(($C_1$-$C_6$)-alkyl)-, —N(phenyl)-, —N(($C_1$-$C_6$)-alkyl-phenyl)-, —N(CO—(CH$_2$)$_{1-10}$—COOH)— and —NH—.

In another embodiment of the invention, one of the radicals R1 or R3 in the compounds of the formula I has the meaning ($C_1$-$C_{30}$)-alkylene-(LAG), wherein at least one carbon atom of the alkylene radical is replaced by aryl or heteroaryl radicals, which are unsubstituted or substituted one, two, or three times by R7; or by ($C_3$-$C_{10}$)-cycloalkyl or heterocycloalkyl radicals, which are unsubstituted or substituted one, two, or three times by R7 and wherein at least one carbon atom of the alkylene radical is optionally replaced by a radical chosen from: —S(O)$_m$— (wherein m=0-2), —O—, —(C=O)—, —N(CH$_3$)—, —N(phenyl)-, —N(CO—(CH$_2$)$_{1-10}$—COOH)— and —NH—.

In another embodiment of the invention, one of the radicals R1 or R3 in the compounds of the formula I has the meaning —(CH$_2$)$_{0-1}$—NH—(C=O)$_{0-1}$—($C_0$-$C_{25}$)-alkylene-(C=O)$_{0-1}$—N(R13)$_{0-1}$-(LAG) or —(CH$_2$)$_{0-1}$-(C=O)$_{0-1}$—NH—($C_0$-$C_{25}$)-alkylene-(C=O)$_{0-1}$—N(R13)$_{0-1}$-(LAG); wherein at least one carbon atom of the alkylene radical is replaced by: aryl or heteroaryl radicals, which are unsubstituted or substituted one, two, or three times by R7; or by ($C_3$-$C_{10}$)-cycloalkyl or heterocycloalkyl radicals, which are unsubstituted or substituted one, two, or three times by R7; and wherein at least one carbon atom of the alkylene radical is optionally replaced by a radical chosen from: oxygen atoms, NH, N(CH$_3$) and SO$_2$, and wherein R13 represents H or CH$_3$.

In another embodiment of the invention, the group LAG in any of the radicals R1 to R6 in the compounds of the invention is a monosugar residue, an acyclic mono-, di- or tricyclic trialkylammoniumalkyl radical, a sulfonic acid or a carboxylic acid.

An aryl radical is to be understood as meaning a phenyl, naphthyl, biphenyl, tetrahydronaphthyl, alpha or beta-tetralone, indanyl or indan-1-onyl radical.

A heteroaryl radical is to be understood as meaning a pyridyl, pyrimidinyl, pyrazinyl, pyridazinyl, pyridazin-3-onyl, pyrrolyl, imidazolyl, pyrazolyl, 1,2,4-triazolyl, indolyl, benzimidazolyl, thienyl, furyl, thiazolyl, oxazolyl, isoxazolyl or isothiazolyl radical.

Heterocycloalkyl radicals are to be understood as meaning ($C_3$-$C_{10}$)-cycloalkyl radicals in which at least one and up to three carbon atoms independently of one another are replaced by NR8, O or S(O)$_m$, wherein m=0-2. Examples include the azetidinyl, pyrrolidinyl, piperidinyl, morpholinyl, 1,4-dioxanyl, tetrahydrofuryl, piperazinyl or thiepanyl radicals.

An acyclic trialkylammonium radical is to be understood as meaning the following group

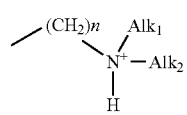

in which n=0 to 10 and Alk$_1$ and Alk$_2$, independently of one another, each denote a straight-chain or branched alkyl radical having 1 to 20 carbon atoms.

An acyclic trialkylammoniumalkyl radical is to be understood as meaning the following group

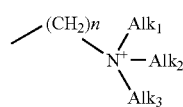

in which n=0 to 10 and Alk$_1$, Alk$_2$, Alk$_3$, independently of one another, each denote a straight-chain or branched alkyl radical having 1 to 20 carbon atoms.

A mono-, di- or tricyclic trialkylammonium radical is to be understood as meaning, for example, radicals such as

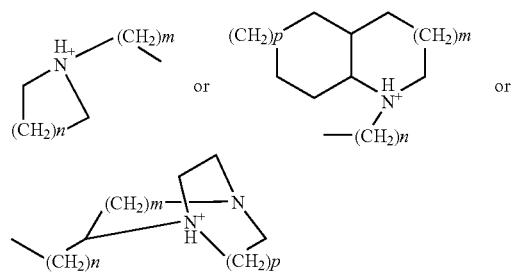

wherein n, m and p, independently of one another, can be 0-10 and wherein one or more CH$_2$ groups, independently of one another, may be replaced by O, S(O)$_m$ (wherein m may be 0-2), NH, N—($C_1$-$C_{10}$)-alkyl, N-phenyl or N—CH$_2$-phenyl.

A mono-, di- or tricyclic trialkylammoniumalkyl radical is to be understood as meaning, for example, radicals such as

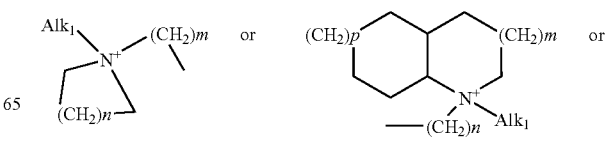

-continued

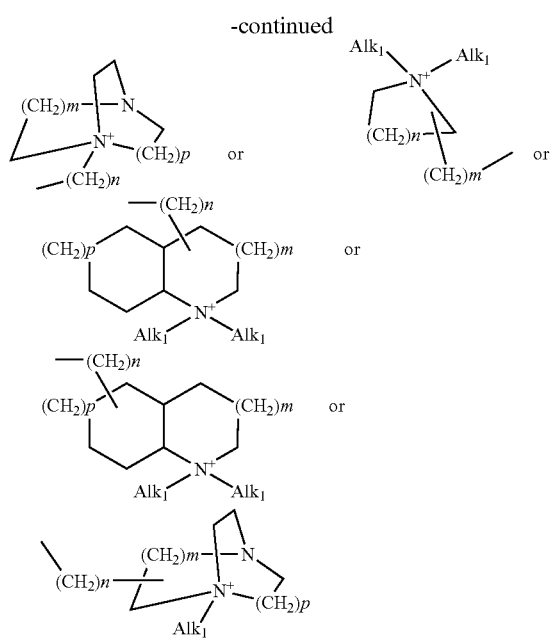

wherein n, m and p, independently of one another, can be 0-10 and wherein one or more $CH_2$ groups independently of one another may be replaced by O, $S(O)_m$ (wherein m may be 0-2), NH, N—$(C_1$-$C_{10})$-alkyl, N-phenyl or N—$CH_2$-phenyl and $Alk_1$ is a straight-chain or branched alkyl radical having 1 to 20 carbon atoms.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the present specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Owing to their increased solubility in water, pharmaceutically acceptable salts are often more suitable for medical applications than the parent compounds. These salts generally have a pharmaceutically acceptable anion or cation. Examples of suitable pharmaceutically acceptable acid addition salts of the compounds according to the invention include salts of inorganic acids, such as hydrochloric acid, hydrobromic acid, phosphoric acid, metaphosphoric acid, nitric acid, sulfonic acid and sulfuric acid, and of organic acids, such as acetic acid, benzenesulfonic acid, benzoic acid, citric acid, ethanesulfonic acid, fumaric acid, gluconic acid, glycolic acid, isothionic acid, lactic acid, lactobionic acid, maleic acid, malic acid, methanesulfonic acid, succinic acid, p-toluenesulfonic acid, tartaric acid and trifluoroacetic acid, for example. An example of an acceptable salt of the compounds of the invention is the chloride salt. Examples of suitable pharmaceutically acceptable basic salts include ammonium salts, alkali metal salts (such as sodium and potassium salts) and alkaline earth metal salts (such as magnesium and calcium salts).

The scope of the invention also includes salts having a pharmaceutically unacceptable anion, which salts may be useful intermediates for preparing or purifying pharmaceutically acceptable salts and/or for use in nontherapeutic, for example in vitro, applications.

Here, the term "derivative having physiological function" refers to any physiologically acceptable derivative of a compound according to the invention, for example an ester, that is able, upon administration to a mammal, for example a human, to form such a compound or an active metabolite (directly or indirectly).

A further aspect of this invention includes prodrugs of the compounds according to the invention. Such prodrugs can be metabolized in vivo to give a compound according to the invention. These prodrugs may or may not be active in their own right.

The compounds according to the invention can also be present in various polymorphic forms, for example as amorphous and crystalline polymorphous forms. Accordingly, another aspect of the invention includes the polymorphic forms of the compounds according to the invention.

Hereinbelow, all references to "compound(s) of the formula (I)" refer to a compound or compounds of the formula (I) as described above, and to their salts, solvates and derivatives having physiological function, as described herein.

The compounds of the formula I and their pharmaceutically acceptable salts and derivatives having physiological function are useful medicaments for treating an impaired lipid metabolism, for example, hyperlipidemia. The compounds of the formula I are also suitable for modulating the serum cholesterol concentration and for preventing and treating arteriosclerotic manifestations.

As used herein, treating or treatment includes the treating of, for example, a patient inflicted with a disease or condition, as well as the prevention, prophylaxis, or protective treatment of a patient. Treatment also includes treating a subject susceptible to or predisposed to developing a disease or condition, which could include patients in whom the disease or condition has not yet presented, as well as patients in whom the disease has been successfully treated but-could redevelop or reoccur.

The compound(s) of the formula (I) can also be administered in combination with other active compounds.

The amount of a compound of the formula (I) required to achieve the desired biological effect depends on a number of factors, for example on the specific compound chosen, on the intended use, on the mode of administration and on the clinical condition of the patient. In general, the daily dose is in the range from 0.1 mg to 100 mg (typically from 0.1 mg to 50 mg) per day per kilogram of bodyweight, for example 0.1-10 mg/kg/day. Tablets or capsules may contain, for example, from 0.01 to 100 mg, typically from 0.02 to 50 mg. In the case of pharmaceutically acceptable salts, the abovementioned weight data relate to the weight of the diphenylazetidinone-ion derived from the salt. An effective amount of a compound of the invention is an amount sufficient to bring about a desired effect. For example, in the context of treating an impaired lipid metabolism, for instance hyperlipidemia, an effective amount of a compound of the invention would constitute an amount sufficient to bring about a beneficial change in the condition of the patient. For the prophylaxis or therapy of the abovementioned conditions, the compounds of the formula (I) can be used by themselves, but they may also be present in the form of a pharmaceutical composition with an acceptable carrier. The carrier must of course be acceptable in the sense that it is compatible with the other constituents of the composition and relatively speaking is not harmful to the health of the patient. The carrier can be a solid or a liquid or both and may be formulated with the compound as an individual dose, for example as a tablet, which can contain from 0.05% to 95% by weight of the active compound. Further pharmaceutically active substances can also be present, including further compounds of the formula (I). The pharmaceutical compositions according to the invention can be prepared by one of the known pharmaceutical methods, which essentially consist in mixing the constituents with pharmacologically acceptable carriers and/or auxiliaries.

Pharmaceutical compositions according to the invention include those which are suitable for oral or peroral (e.g. sublingual) administration, although the most suitable manner of administration is dependent in each individual case on the nature and severity of the condition to be treated and on the type of the compound of the formula (I) used in each case. Coated formulations and coated delayed-release formulations are also included in the scope of the invention, as areacid-resistant and enteric formulations. Examples of suitable enteric coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration can be present in separate units, such as, for example, capsules, cachets, lozenges or tablets, which in each case contain a specific amount of the compound of the formula (I); as a powder or granules; as a solution or suspension in an aqueous or nonaqueous liquid; or as an oil-in-water or water-in-oil emulsion. As already mentioned, these compositions can be prepared according to any suitable pharmaceutical method that includes a step in which the active compound and the carrier (which can consist of one or more additional constituents) are brought into contact. In general, the compositions are prepared by uniform and homogeneous mixing of the active compound with a liquid and/or finely divided solid carrier, after which the product, if necessary, is shaped. For example, a tablet can thus be prepared by pressing or shaping a powder or granules of the compound, if appropriate with one or more additional constituents. Pressed tablets can be produced by tableting the compound in free-flowing form, such as, for example, a powder or granules, if appropriate mixed with a binder, lubricant, inert diluent and/or a (number of) surface-active/dispersing agent(s) in a suitable machine. Shaped tablets can be produced by shaping the pulverulent compound moistened with an inert liquid diluent in a suitable machine.

Pharmaceutical compositions suitable for peroral (sublingual) administration include lozenges which contain a compound of the formula (I) with a flavoring, customarily sucrose and gum arabic or tragacanth, and pastilles which include the compound in an inert base such as gelatin and glycerol or sucrose and gum arabic.

Other suitable other active compounds for the combination preparations include, but are not limited to:

all antidiabetics mentioned in Rote Liste 2001, Chapter 12. They can be combined with the compounds of the formula I according to the invention to achieve a synergistically enhanced action. The active compound combination can be administered either by separate administration of the active compounds to the patient or in the form of combination preparations comprising a plurality of active compounds in a pharmaceutical preparation.

Antidiabetics include insulin and insulin derivatives, such as, for example, Lantus® or HMR 1964, GLP-1 derivatives, such as, for example, those disclosed by Novo Nordisk A/S in WO 98/08871, and oral hypoglycemic active compounds.

Examples of oral hypoglycemic active compounds include sulfonylureas, biguadines, meglitinides, oxadiazolidinediones, thiazolidinediones, glucosidase inhibitors, glucagon antagonists, GLP-1 agonists, potassium channel openers, such as, for example, those disclosed by Novo Nordisk A/S in WO 97/26265 and WO 99/03861, insulin sensitizers, inhibitors of liver enzymes involved in stimulating gluconeogenesis and/or glycogenolysis, modulators of glucose uptake, compounds which modulate lipid metabolism, such as antihyperlipidemic active compounds and antilipidemic active compounds, compounds that reduce food intake, PPAR and PXR agonists and active compounds that act on the ATP-dependent potassium channel of the beta cells.

In one embodiment of the invention, the compounds of the formula I are administered in combination with an HMGCOA reductase inhibitor such as simvastatin, fluvastatin, pravastatin, lovastatin, atorvastatin, cerivastatin, or rosuvastatin.

In another embodiment of the invention, the compounds of the formula I are administered in combination with a cholesterol absorption inhibitor, such as, for example, ezetimibe, tiqueside, or pamaqueside.

In another embodiment of the invention, the compounds of the formula I are administered in combination with a PPAR gamma agonist, such as, for example, rosiglitazone, pioglitazone, JTT-501, or GI 262570.

In another embodiment of the invention, the compounds of the formula I are administered in combination with a PPAR alpha agonist, such as, for example, GW 9578, or GW 7647.

In another embodiment of the invention, the compounds of the formula I are administered in combination with a mixed PPAR alpha/gamma agonist, such as, for example, GW 1536, AVE 8042, AVE 8134, or AVE 0847.

In another embodiment of the invention, the compounds of the formula I are administered in combination with a fibrate, such as, for example, fenofibrate, clofibrate, or bezafibrate.

In another embodiment of the invention, the compounds of the formula I are administered in combination with an MTP inhibitor, such as, for example, Bay 13-9952, BMS-201038, or R-103757.

In another embodiment of the invention, the compounds of the formula I are administered in combination with a bile acid absorption inhibitor, such as, for example, HMR 1453.

In another embodiment of the invention, the compounds of the formula I are administered in combination with a CETP inhibitor, such as, for example, Bay 194789.

In another embodiment of the invention, the compounds of the formula I are administered in combination with a polymeric bile acid adsorber, such as, for example, cholestyramine, or colesolvam.

In another embodiment of the invention, the compounds of the formula I are administered in combination with an LDL receptor inducer, such as, for example, HMR1171, or HMR1586.

In another embodiment of the invention, the compounds of the formula I are administered in combination with an ACAT inhibitor, such as, for example, avasimibe.

In another embodiment of the invention, the compounds of the formula I are administered in combination with an antioxidant, such as, for example, OPC-14117.

In another embodiment of the invention, the compounds of the formula I are administered in combination with a lipoprotein lipase inhibitor, such as, for example, NO-1886.

In another embodiment of the invention, the compounds of the formula I are administered in combination with an ATP citrate lyase inhibitor, such as, for example, SB-204990.

In another embodiment of the invention, the compounds of the formula I are administered in combination with a squalene synthetase inhibitor, such as, for example, BMS-188494.

In another embodiment of the invention, the compounds of the formula I are administered in combination with a lipoprotein(a) antagonist, such as, for example, CI-1027 or nicotinic acid.

In another embodiment of the invention, the compounds of the formula I are administered in combination with a lipase inhibitor, such as, for example, Orlistat.

In another embodiment of the invention, the compounds of the formula I are administered in combination with insulin.

In another embodiment, the compounds of the formula I are administered in combination with a sulfonylurea, such as, for example, tolbutamide, glibenclamide, glipizide or gliclazide.

In another embodiment, the compounds of the formula I are administered in combination with a biguanide, such as, for example, metformin.

In another embodiment, the compounds of the formula I are administered in combination with a meglitinide, such as, for example, repaglinide.

In another embodiment, the compounds of the formula I are administered in combination with a thiazolidinedione, such as, for example, troglitazone, ciglitazone, pioglitazone, rosiglitazone, or the compounds disclosed by Dr. Reddy's Research Foundation in WO 97/41097, for example 5-[[4-[(3, 4-dihydro-3-methyl4-oxo-2-quinazolinylmethoxy]phenyl]methyl]-2,4-thiazolidinedione.

In another embodiment, the compounds of the formula I are administered in combination with an α-glucosidase inhibitor, such as, for example, miglitol or acarbose.

In another embodiment, the compounds of the formula I are administered in combination with an active compound that acts on the ATP-dependent potassium channel of beta cells, such as, for example, tolbutamide, glibenclamide, glipizide, gliazide or repaglinide.

In another embodiment, the compounds of the formula I are administered in combination with more than one of the abovementioned compounds, for example in combination with a sulfonylurea and mefformin, a sulfonylurea and acarbose, repaglinide and metformin, insulin and a sulfonylurea, insulin and mefformin, insulin and troglitazon, or insulin and lovastatin, etc.

In a further embodiment, the compounds of the formula I are administered in combination with CART agonists, NPY agonists, MC3 and MC4 agonists, orexin agonists, H3 agonists, TNF agonists, CRF agonists, CRF BP antagonists, urocortin agonists, β3-agonists, MCH (melanine-concentrating hormone) antagonists, CCK agonists, serotonin reuptake inhibitors, mixed serotonin and noradrenergic compounds, 5HT agonists, bombesin agonists, galanin antagonists, growth hormone, growth hormone-releasing compounds, TRH agonists, decoupling protein 2 or 3 modulators, leptin agonists, DA agonists (bromocriptine, doprexin), lipase/amylase inhibitors, PPAR modulators, RXR modulators or TR-β agonists.

In another embodiment of the invention, the further active compound is leptin.

In another embodiment, the further active compound is dexamphetamine or amphetamine.

In another embodiment, the further active compound is fenfluramine or dexfenfluramine.

In another embodiment, the further active compound is sibutramine.

In another embodiment, the further active compound is Orlistat.

In another embodiment, the further active compound is mazindol or phentermine.

In another embodiment, the compounds of the formula I are administered in combination with fiber, for example insoluble fiber, such as, for example, Caromax®. The combination with Caromax® can be administered in a single preparation or by separate administration of compounds of the formula I and Caromax®. Here, Caromax® can also be administered in the form of food, such as, for example, in bakery goods or muesli bars. Compared to the individual active compounds, the combination of compounds of the formula I with Caromax® is, in addition to providing an enhanced action, also characterized by its improved tolerability, for example with respect to the lowering of LDL cholesterol.

It goes without saying that each suitable combination of the compounds according to the invention with one or more of the compounds mentioned above and optionally one or more further pharmacologically active substances is included in the scope of the present invention.

The scope of the invention also includes both, stereoisomer mixtures of the formula I and the pure stereoisomers of the formula I, as well as diastereomer mixtures of compounds of the formula I and the pure diastereomers. The mixtures may, for example, be separated by known chromatographic means.

One embodiment of the invention includes both, racemic and enantiomerically pure compounds of the formula I of the following structure:

Sugar residues are to be understood as meaning, for example, compounds derived from aldoses and ketoses that have 3 to 7 carbon atoms and that may belong to the D or the L series; also included are amino sugars, sugar alcohols or sugar acids. Glucose, mannose, fructose, galactose, ribose, erythrose, glycerolaldehyde, sedoheptulose, glucosamine, galactosamine, glucuronic acid, galacturonic acid, gluconic acid, galactonic acid, mannonic acid, glucamine, 3-amino-1, 2-propanediol, glucaric acid and galactaric acid may be mentioned by way of example.

Disugars are saccharides composed of two sugar units. Di-, tri- or tetrasaccharides are formed by acetal-like binding of two or more sugars. Here, the bonds may be in the α- or β-form. Lactose, maltose and cellobiose may be mentioned by way of example.

If the sugar is substituted, the substitution may take place at the hydrogen atom of an OH group of the sugar.

Examples of suitable protective groups for the hydroxyl groups of the sugars include: benzyl, acetyl, benzoyl, pivaloyl, trityl, tert-butyidimethylsilyl, benzylidene, cyclohexylidene or isopropylidene protective groups.

The term "amino acids" or "amino acid residues" refers, for example, to the stereoisomeric forms, i.e. the D or L forms, of, for example, the following compounds:

| | | |
|---|---|---|
| alanine | glycine | proline |
| cysteine | histidine | glutamine |
| aspartic acid | isoleucine | arginine |
| glutamic acid | lysine | serine |
| phenylalanine | leucine | threonine |
| tryptophan | methionine | valine |
| tyrosine | asparagine | |
| 2-aminoadipic acid | 2-aminoisobutyric acid | |
| 3-aminoadipic acid | 3-aminoisobutyric acid | |
| beta-alanine | 2-aminopimelic acid | |
| 2-aminobutyric acid | 2,4-diaminobutyric acid | |
| 4-aminobutyric acid | desmosine | |
| piperidine carboxylic acid | 2,2-diaminopimelic acid | |
| 6-aminocaproic acid | 2,3-diaminopropionic acid | |
| 2-aminoheptanoic acid | N-ethylglycine | |
| 2-(2-thienyl)glycine | 3-(2-thienyl)alanine | |
| penicillamine | sarcosine | |
| N-ethylasparagine | N-methylisoleucine | |
| hydroxylysine | 6-N-methyllysine | |
| allo-hydroxylysine | N-methylvaline | |
| 3-hydroxyproline | norvaline | |
| 4-hydroxyproline | norleucine | |
| isodesmosine | ornithine | |
| allo-isoleucine | | |
| N-methylglycine | | |

For abbreviating the amino acids, the conventional notation was used (cf. Schröder, Lübke, The Peptides, Volume I, New York 1965, pages XXII-XXIII; Houben-Weyl, Methoden der Organischen Chemie [Methods of organic chemistry], Volume XV/1 and 2, Stuttgart 1974). The amino acid pGlu denotes pyroglutamyl, Nal denotes 3-(2-naphthyl)alanine, azagly-$NH_2$ denotes a compound of the formula $NH_2$—NH—$CONH_2$ and D-Asp denotes the D form of aspartic acid. According to their chemical nature, peptides are acid amides, and on hydrolysis they decompose into amino acids.

An oligopeptide is to be understood as meaning a peptide constructed of 2 to 9 of the amino acids mentioned above.

Examples of suitable protective groups (see, for example, T. W. Greene, "Protective Groups in Organic Synthesis") for amino acids include:

Arg(Tos), Arg(Mts), Arg(Mtr), Arg(PMV), Asp(OBzl), Asp(OBut), Cys(4-MeBzl), Cys(Acm), Cys(SBut), Glu (Obzl), Glu(Obut), His(Tos), His(Fmoc), His(Dnp), His(Trt), Lys(Cl-Z), Lys(Boc), Met(O), Ser(Bzl), Ser(But), Thr(Bzl), Thr(But), Trp(Mts), Trp(CHO), Tyr(Br-Z), Tyr(Bzl) or Tyr (But).

Examples of amino protective groups that may be used include the benzyloxycarbonyl (Z) radical, which can be removed by catalytic hydrogenation; the 2-(3,5-dimethyloxyphenyl)propyl(2)oxycarbonyl(Ddz) or trityl (Trt) radical, which can be removed by weak acids; the t-butylcarbamate (BOC) radical, which can be removed by 3M hydrochloric acid; and the 9-fluorenylmethyloxycarbonyl (Fmoc) radical, which can be removed using secondary amines.

Another embodiment of the invention relates to a process for preparing diphenylazetidinone derivatives of formula I.

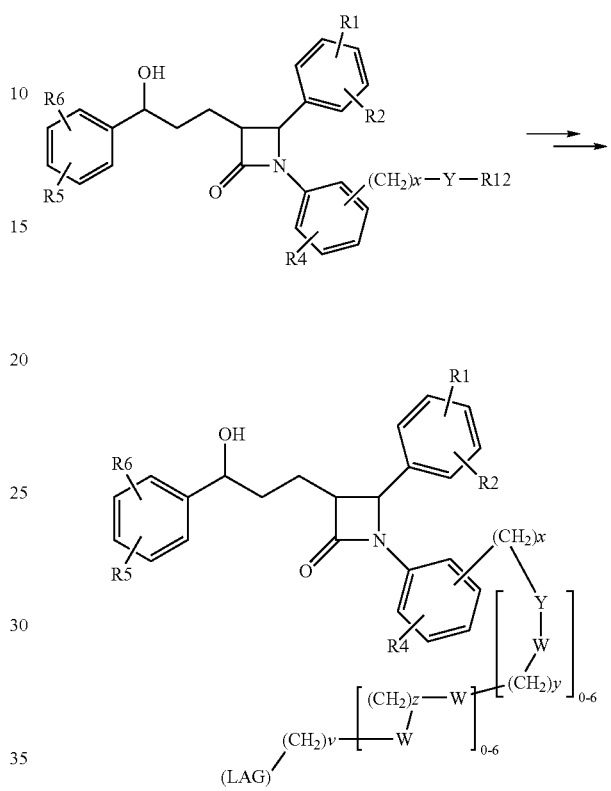

Y can be S, O, (C=O), (C=S), CH=CH, C≡C, N((C1-C6)-alkyl), N(phenyl), N((C1-C6)-alkyl-phenyl), N(CO—(CH2)1-10-COOH) or NH;

R12 can be H or, if Y=(C=O) or (C=S), then R12 can be OH;

W can, independently of Y, be an aryl or heteroaryl radical, unsubstituted, or mono-, di-, or trisubstituted; or a (C3-C10)-cycloalkyl or heterocycloalkyl radical, unsubstituted, or mono-, di-, tri-, or tetrasubstituted; or —S(O)$_m$— (wherein m=0-2), —O—, —(C=O)—, —(C=S)—, —CH=CH—, —C≡C—, —N((C1-C6)-alkyl)-, —N(phenyl), —N((C1-C6)-alkyl-phenyl)-, —N(CO—(CH2)1-10-COOH)— or —NH— or a bond;

v, x, y and z, independently of one another, can be 0 to 10.

In compound II, (CH)x-Y-R12 can alternatively also be attached to one of the other two phenyl rings.

The process for preparing compounds of the formula I comprises, for example, reacting an amine of the formula II with an alkylating or acylating agent which, may carry a further functionality (for example in the omega position), if appropriate in protected form. This functionality may be used (after deprotection) for attaching (LAG), for example with the formation of ether, amine or amide bonds.

The examples below serve to illustrate the invention in more detail, without limiting the invention to the products and embodiments described in the examples.

EXAMPLE I 2,3,4,5,6-Pentahydroxyhexylamide of 4-(4-{4-[3-[3-(4-fluorophenyl)-3-hydroxypropyl]-2-(4-methoxyphenyl)-4-oxoazetidin-1-yl]benzylcarbamoyl}phenoxy)benzoic acid (7)

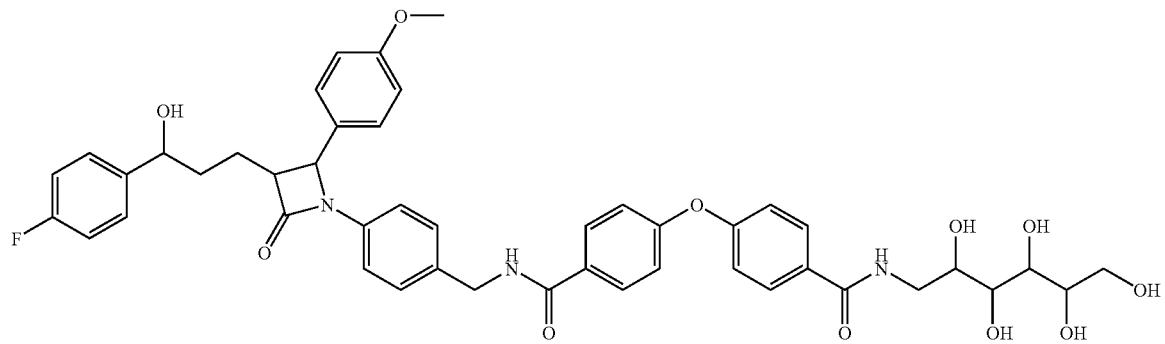

a) 3-[5-(tert-butyldimethylsilanyloxy)-5-(4-fluorophenyl)-pentanoyl]-4-phenyl-oxazolidin-2-one (1)

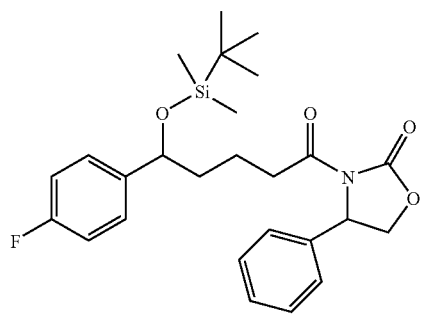

27 g of 3-[5-(4-fluorophenyl)-5-hydroxypentanoyl]4-phenylazolidin-2-one, 13.6 g of tert-butyldimethylsilyl chloride and 10.2 g of imidazole were dissolved in 36 ml of dimethylformamide and stirred at 60° C. for 90 min. After the reaction ended, the mixture was dissolved in ethyl acetate and extracted two times with water. The organic phase was dried over magnesium sulfate, filtered and concentrated under reduced pressure. This produced 3-[5-(tert-butyidimethylsilanyloxy)-5-(4-fluorophenyl)-pentanoyl]-4-phenyloxazolidin-2-one (1) of molecular weight 471.65 (C26H34FNO4Si); MS (ESI): 340.28 (MH+-HOSi(CH3)2C(CH3)3).

b) 4-[5-(tert-butyidimethylsilanyloxy)-5-(4-fluorophenyl)-1-(4-methoxyphenyl)-2-(2-oxo-4-phenyloxazolidine-3-carbonyl)pentylamino]benzonitrile (2)

16.2 g of 3-[5-(tert-butyldimethylsilanyloxy)-5-(4-fluorophenyl)-pentanoyl]-4-phenyloxazolidin-2-one (1) were dissolved in 350 ml of dichloromethane. 19.8 ml of Hünig base and 10.14 g of 4-[(4-methoxyphenylimino)methyl]benzonitrile were added, and the solution was cooled to −10° C. 8.52 ml of trimethylsilyl triflate were added to the cooled solution, and the mixture was stirred at −10° C. for 30 min. The solution was then cooled to −30° C., and 44 ml of titanium tetrachloride solution were added. The reaction mixture was stirred at a temperature ranging from −30 to −40° C. for 2 h. The solution was then allowed to warm to room temperature and the reaction solution was washed successively with 200 ml of 2N sulfuric acid, 300 ml of 20% strength sodium hydrogen sulfite solution and sat. sodium chloride solution. The organic phase was dried over magnesium sulfate, concentrated under reduced pressure, and the residue was purified on silica gel using n-heptane/ethyl acetate 3/1. This produced 4-[5-(tert-butyldimethylsilanyloxy)-5-(4-fluorophenyl)-1-(4-methoxyphenyl)-2-(2-oxo-4-phenyloxazolidine-3-carbonyl)pentylamino]benzonitrile (2) of molecular weight 707.93 (C41H46FN3O5Si); MS (ESI): 590.51 (MH+-C7H5N2).

c) 4-[3-[3-(tert-butyidimethylsilanyloxy)-3-(4-fluorophenyl)propyl]-2-(4-methoxyphenyl)-4-oxoazetidin-1-yl]benzonitrile (3)

13.2 g of 4-[5-(tert-butyldimethylsilanyloxy)-5-(4-fluorophenyl)-1-(4-methoxyphenyl)-2-(2-oxo-4-phenyloxazolidine-3-carbonyl)pentylamino]benzonitdle (2) were dissolved in 380 ml of methyl tert-butylether. 18.6 ml of N,O-bis(trimethylsilyl)acetamide and 1.86 ml of a 1 M solution of tetrabutylammonium fluoride in tetrahydrofuran were added and the mixture was stirred at room temperature for 2 h. After the reaction ended, 10 ml of acetic acid were added, the reaction mixture was concentrated under reduced pressure and the residue was purified on silica gel using toluene/ethyl acetate 50/1. This produced 4-[3-[3-(tert-butyldimethylsilanyloxy)-3-(4-fluorophenyl)propyl]-2-(4-methoxyphenyl)-4-oxoazetidin-1-yl]-benzonitrile (3) of molecular weight 544.75 (C32H37FN2O3Si); MS (ESI): 545.56 (M+H+).

d) 4-[3-[3-(4-Fluorophenyl)-3-hydroxypropyl]-2-(4-methoxyphenyl)-4-oxoazetidin-1-yl]-benzonitrile (4)

3.5 g of 4-[3-[3-(tert-butyidimethylsilanyloxy)-3-(4-fluorophenyl)propyl]-2-(4-methoxyphenyl)-4-oxoazetidin-1-yl]-benzonitrile (3) were dissolved in 65 ml of tetrahydrofuran. 0.74 ml of acetic acid and 8.03 ml of a 1 M solution of tetrabutylammonium fluoride in tetrahydrofuran were added and the mixture was stirred at room temperature for 2 h. Another 4.82 ml of the tetrabutylammonium fluoride solution were then added, and the mixture was stirred at reflux temperature for another 3 h. The cooled reaction mixture was concentrated under reduced pressure and the residue was purified by silica gel chromatography using n-heptane/ethyl acetate 2/1. This produced 4-[3-[3-(4-fluorophenyl)-3-hydroxypropyl]-2-(4-methoxyphenyl)-4-oxoazetidin-1-yl]-benzonitrile (4) of molecular weight 430.48 (C26H23FN2O3); MS (ESI): 431.24 (M+H+).

e) 1-(4-Aminomethylphenyl)-3-[3-(4-fluorophenyl)-3-hydroxypropyl]4-(4-methoxyphenyl)-azetidin-2-one (5)

1.22 g of 4-[3-[3-(4-fluorophenyl)-3-hydroxypropyl]-2-(4-methoxyphenyl)-4-oxoazetidin-1-yl]-benzonitrile (4) were dissolved in 90 ml of ethanol. 10 ml of conc. ammonia solution and an excess of Raney nickel were added, and the mixture was stirred at 60° C. and a hydrogen pressure of 10 bar for 8 h. Overnight, the reaction mixture cooled to room temperature. The next day, the catalyst was removed, the filtrate was concentrated under reduced pressure and the residue was purified by silica gel chromatography using dichloromethane/methanol/ammonia solution 10/1/0.1. This produced 1-(4-aminomethylphenyl)-3-[3-(4-fluorophenyl)-3-hydroxypropyl]4-(4-methoxyphenyl)-azetidin-2-one (5) of molecular weight 434.51 (C26H27FN2O3); MS (ESI): 418.2 (MH+-NH3).

f) 2,3,4,5,6-Pentahydroxyhexylamide of 4,4'-oxybisbenzoic acid (6)

At room temperature, 0.52 g of 4,4'-oxybisbenzoic acid and 0.36 g of D-glucamine were suspended in 10 ml of dry dimethylformamide. 0.31 g of HOBt and 0.39 g of EDC were added and the mixture was stirred at room temperature for 12 h. The reaction mixture was evaporated to dryness and dried under high vacuum. The residue was thoroughly titrated with water, the resulting suspension was filtered and the residue was titrated with methanol and filtered again. The filtrate was concentrated to half of its volume using a rotary evaporator, and the solution was cooled in an ice bath. The resulting precipitate was filtered off with suction, washed with a little ice-cooled methanol and dried under reduced pressure. This produced 2,3,4,5,6-pentahydroxyhexylamide of 4,4'-oxybisbenzoic acid (6) of molecular weight 421.40 (C20H23NO9); MS (ESI): 422.28 (MH+).

g) 2,3,4,5,6-Pentahydroxyhexylamide of 4-(4-{4-[3-[3-(4-fluorophenyl)-3-hydroxypropyl]-2-(4-methoxyphenyl)-4-oxoazetidin-1-yl]benzylcarbamoyl}phenoxy)benzoic acid (7):

87 mg of the compound prepared under e) and 90 mg of the compound prepared under f) were dissolved at room temperature in 3 ml of dry dimethylformamide. 31 mg of HOBt and 39 mg of EDC were added and the mixture was stirred at room temperature for 12 h. The reaction mixture was evaporated to dryness under high vacuum and the residue was titrated with dichloromethane, filtered off with suction, washed with dichloromethane and dried under reduced pressure. This produced the 2,3,4,5,6-pentahydroxyhexylamide of 4-(4-{4-[3-[3-(4-fluorophenyl)-3-hydroxypropyl]-2-(4-methoxyphenyl)-4-oxoazetidin-1-yl]benzylcarbamoyl}phenoxy)benzoic acid (7) with a molecular weight 837.90 (C46H48FN3O11); MS (ESI): 838,39 (MH+).

EXAMPLE II 2,3,4,5,6-Pentahydroxyhexylamide of 4-(4-{4-[3-(3-hydroxy-3-phenylpropyl)-2-oxo-4-phenylazetidin-1-yl]benzylcarbamoyl}phenoxy)benzoic acid (9):

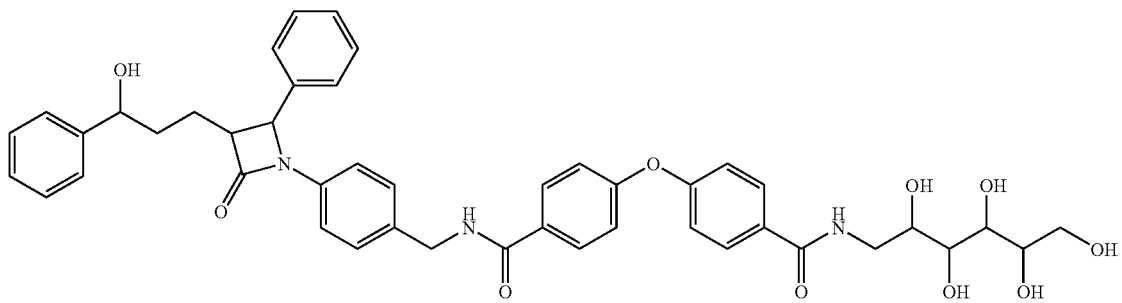

a) 1-(4-Aminomethylphenyl)-3-(3-hydroxy-3-phenylpropyl)-4-phenylazetidin-2-one (8):

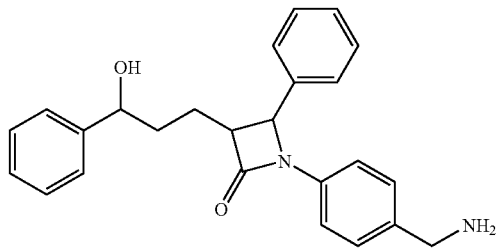

This compound was prepared as described above for 1-(4-aminomethylphenyl)-3-[3-(4-fluorophenyl)-3-hydroxypropyl]4-(4-methoxyphenyl)-azetidin-2-one, except that 3-[5-(tert-butyldimethylsilanyloxy)-5-phenylpentanoyl]4-phenyloxazolidin-2-one and 4-(benzylideneamino)benzonitrile were used. This produced 1-(4-aminomethylphenyl)-3-(3-hydroxy-3-phenylpropyl)-4-phenylazetidin-2-one (8) of molecular weight 386.50 (C25H26N2O2); MS (ESI): 370.2 (MH+-NH3).

b) 2,3,4,5,6-Pentahydroxyhexylamide of 4-(4-{4-[3-(3-hydroxy-3-phenylpropyl)-2-oxo-4-phenylazetidin-1-yl]benzylcarbamoyl}phenoxy)benzoic acid (9)

The benzylamine from IIa was reacted with the 2,3,4,5,6-pentahydroxyhexylamide of 4,4'-oxybisbenzoic acid from If as described in Example I. This produced the 2,3,4,5,6-pentahydroxyhexylamide of 4-(4-{4-[3-(3-hydroxy-3-phenyl-propyl)-2-oxo4-phenylazetidin-1-yl]benzylcarbamoyl}phenoxy)benzoic acid (9) of molecular weight 789.89 (C45H47N3O10); MS (ESI): 790.26 (MH+).

EXAMPLE III 2,3,4,5,6-Pentahydroxyhexylamide of 4-(4-{4-[3-[3-(4-fluorophenyl)-3-hydroxypropyl]-2-(4-methoxyphenyl)-4-oxoazetidin-1-yl]-benzylcarbamoyl}-benzyl)-benzoic acid (10)

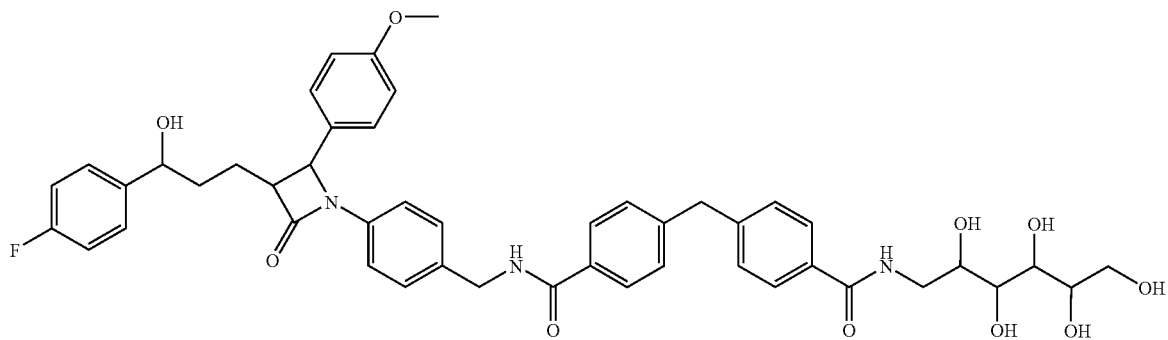

The compound of Example III was obtained analogously to the procedure of Example I, except that the 2,3,4,5,6-pentahydroxyhexylamide of diphenylmethane-4,4'-dicarboxylic acid was used. This produced the 2,3,4,5,6-pentahydroxyhexylamide of 4-(4-{4-[3-[3-(4-fluorophenyl)-3-hydroxypropyl]-2-(4-methoxyphenyl)-4-oxoazetidin-1-yl]-benzylcarbamoyl}benzyl)benzoic acid (10) of molecular weight 835.93 (C47H50FN3O10); MS (ESI): 836.18 (MH+).

EXAMPLE IV

1-[4-(4{-1-(4-Fluorophenyl)-3-[3-(4-fluorophenyl)-3-hydroxypropyl]-4-oxoazetidin-2-yl}phenoxymethyl)benzyl]-4-aza-1-azoniabicyclo[2.2.2]octane bromide (13)

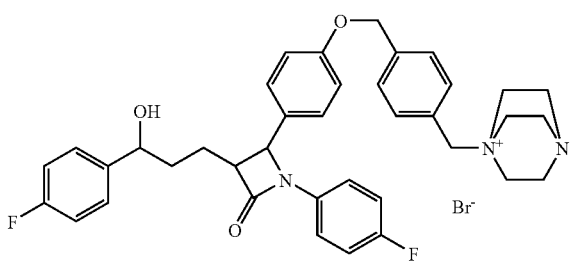

a) 4-[4-(4-Bromomethylbenzyloxy)phenyl]-1-(4-fluorophenyl)-3-[3-(4-fluorophenyl)-3-hydroxypropyl]azetidin-2-one (12)

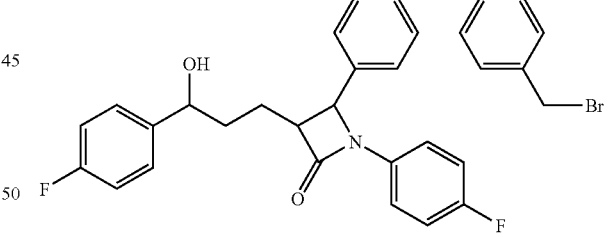

3.0 g of 1-(4-fluorophenyl)-3-[3-(4-fluorophenyl)-3-hydroxypropyl]-4-(4-hydroxyphenyl)-azetidin-2-one (11) 7.0 g of 1,4-bisbromomethylbenzene and 5.0 g of potassium carbonate were dissolved in 100 ml of dimethylformamide and stirred at room temperature for 90 min. After the reaction ended, the mixture was dissolved in ethyl acetate and extracted two times with water. The organic phase was dried over magnesium sulfate, filtered and concentrated under reduced pressure. The residue was purified by flash chromatography (n-heptane/ethyl acetate). Yield 3.2 g of colorless crystals (12) of molecular weight 592.49 (C32H28BrF2NO3); MS (ESI): 592.2 (MH+).

b) 1-[4-(4-{1-(4-Fluorophenyl)-3-[3-(4-fluorophenyl)-3-hydroxypropyl]-4-oxoazetidin-2-yl}phenoxymethyl)benzyl]-4-aza-1-azoniabicyclo[2.2.2]octane bromide (13)

180 mg of (12) and 300 mg of 1,4-diazabicyclo[2.2.2]octane (DABCO) were dissolved in 5 ml of toluene and stirred at 80° C. for 90 min. After the reaction ended, the mixture was allowed to cool and the colorless solid was filtered off with suction. This gave 195 mg of product (13) of molecular weight 704.66 (C38H40BrF2N3O3); MS (ESI): 624.30 (MH+).

EXAMPLE V 1-(4-Fluorophenyl)-3-[3-(4-fluorophenyl)-3-hydroxypropyl]-4-(4-{4-[(2,3,4,5,6-pentahydroxyhexylamine)methyl]benzyloxy}phenyl)azetidin-2-one (14)

a) 4-[4-(2-Bromomethyl benzyloxy)phenyl]-1-(4-fluorophenyl)-3-[3-(4-fluorophenyl)-3-hydroxypropyl]-azetidin-2-one (15)

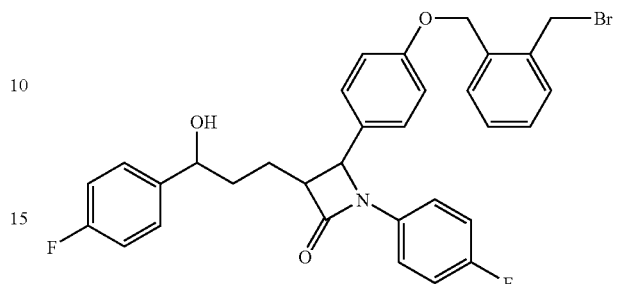

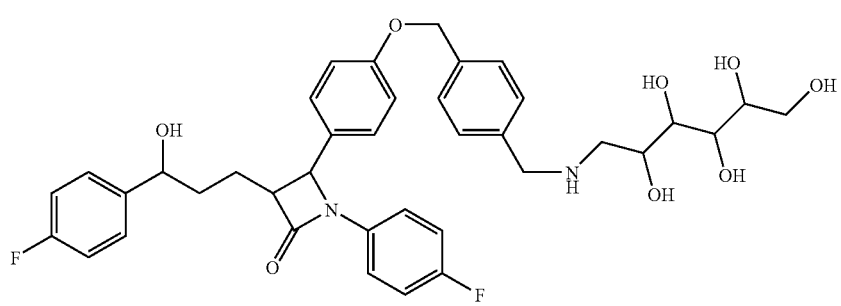

60 mg of (12) and 150 mg of glucamine were dissolved in 5 ml of dimethylformamide and stirred at 80° C. for 90 min. After the reaction ended, the mixture was dissolved in ethyl acetate and extracted two times with water. The organic phase was dried over magnesium sulfate, filtered, and concentrated under reduced pressure. The residue was purified by flash chromatography (methylene chloride/methanol/conc. ammonia 30/10/3). Yield 33 mg of a colorless solid (14) of molecular weight 692.76 (C38H42F2N2O8); MS (ESI): 693.5 (MH+).

1-(4-Fluorophenyl)-3-[3-(4-fluorophenyl)-3-hydroxypropyl]4-(4-hydroxyphenyl)-azetidin-2-one (11) was reacted with 1,2-bisbromomethylbenzene and potassium carbonate analogously to Example IV, giving a colorless solid (15) of molecular weight 592.49 (C32H28BrF2NO3); MS (ESI): 592.2 (MH+).

EXAMPLE VI

1-[2-(4-{1-(4-Fluorophenyl)-3-[3-(4-fluorophenyl)-3-hydroxypropyl]-4-oxoazetidin-2-yl}phenoxymethyl)benzyl]4-aza-1-azoniabicyclo[2.2.2]octane bromide (16)

b) 1-[4-(4-{1-(4-Fluorophenyl)-3-[3-(4-fluorophenyl)-3-hydroxypropyl]-4-oxoazetidin-2-yl}phenoxymethyl)benzyl]-4-aza-1-azoniabicyclo[2.2.2]octane bromide (16)

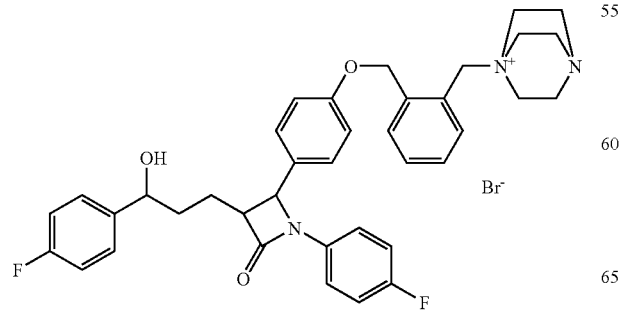

Compound (15) and DABCO were dissolved in toluene and reacted analogously to Example IV, giving the product (16) as a colorless solid of molecular weight 704.66 (C38H40BrF2N3O3); MS (ESI): 624.30 (MH+).

EXAMPLE VII 1-(4-Fluorophenyl)-3-[3-(4-fluorophenyl)-3-hydroxypropyl]-4-(4-{2-[(2,3,4,5,6-pentahydroxyhexylamine)methyl]benzyloxy}phenyl)azetidin-2-one (17)

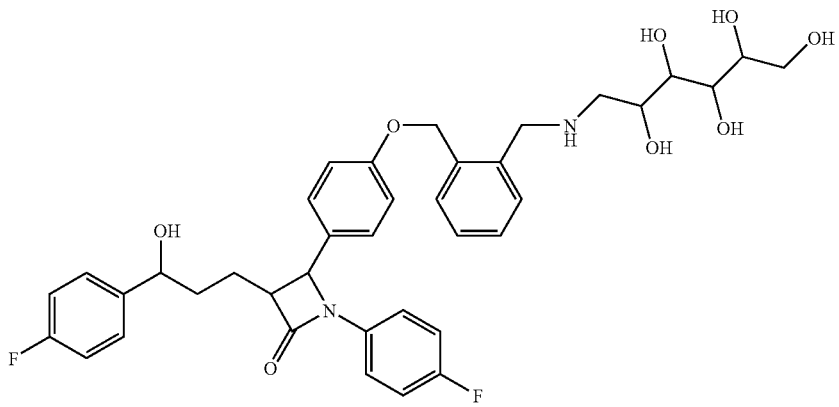

Compound (15) and glucamine were dissolved in dimethylformamide and reacted analogously to Example V, giving the product (17) as a colorless solid of molecular weight 692.76 (C38H42F2N2O8); MS (ESI): 693.5 (MH+).

EXAMPLE VIII

1-[3-(4-{1-(4-Fluorophenyl)-3-[3-(4-fluorophenyl)-3-hydroxypropyl]-4-oxoazetidin-2-yl}phenoxymethyl)benzyl]-4-aza-1-azoniabicyclo[2.2.2]octane bromide (19)

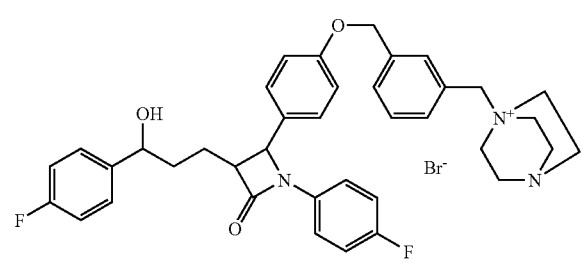

a) 4-[4-(3-Bromomethylbenzyloxy)phenyl]-1-(4-fluorophenyl)-3-[3-(4-fluorophenyl)-3-hydroxypropyl]azetidin-2-one (18)

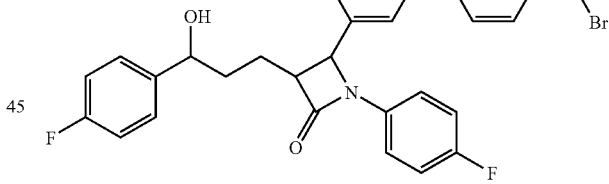

1-(4-Fluorophenyl)-3-[3-(4-fluorophenyl)-3-hydroxypropyl]4-(4-hydroxyphenyl)azetidin-2-one (11) was reacted with 1,3-bisbromomethylbenzene and potassium carbonate analogously to Example IV, giving a colorless solid (18) of molecular weight 592.49 (C32H28BrF2NO3); MS (ESI): 592.2 (MH+).

b) 1-[3-(4-{1-(4-Fluorophenyl)-3-[3-(4-fluorophenyl)-3-hydroxypropyl]-4-oxoazetidin-2-yl}phenoxymethyl)benzyl]-4-aza-1-azoniabicyclo[2.2.2]octane bromide (19)

Compound (18) and DABCO were dissolved in toluene and reacted analogously to Example IV, giving the product (19) as a colorless solid of molecular weight 704.66 (C38H40BrF2N3O3); MS (ESI): 624.30 (MH+).

EXAMPLE IX 1-(4-Fluorophenyl)-3-[3-(4-fluorophenyl)-3-hydroxypropyl]-4-(4-{3-[(2,3,4,5,6-pentahydroxyhexylamine)methyl]benzyloxy}phenyl)azetidin-2-one (20)

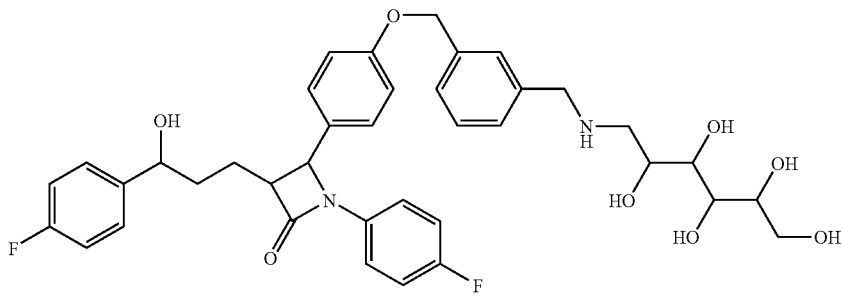

Compound (18) and glucamine were dissolved in dimethylformamide and reacted analogously to Example V, giving the product (20) as a colorless solid of molecular weight 692.76 (C38H42F2N2O8); MS (ESI): 693.5 (MH+).

EXAMPLE X

1-[4'-(4-{1-(4-Fluorophenyl)-3-[3-(4-fluorophenyl)-3-hydroxypropyl]-4-oxoazetidin-2-yl}phenoxymethyl)biphenyl-4-ylmethyl]-4-aza-1-azoniabicyclo[2.2.2]octane bromide (22)

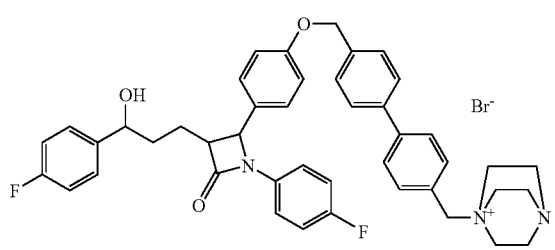

a) 4-[4-(4'-Bromomethylbiphenyl-4-ylmethoxy)phenyl]-1-(4-fluorophenyl)-3-[3-(4-fluorophenyl)-3-hydroxypropyl]azetidin-2-one (21)

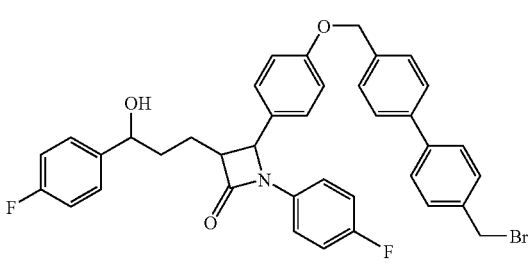

1-(4-Fluorophenyl)-3-[3-(4-fluorophenyl)-3-hydroxypropyl]-4-(4-hydroxyphenyl)-azetidin-2-one (11) was reacted with 4,4'-bisbromomethylbiphenyl and potassium carbonate analogously to Example IV, giving a colorless solid (21) of molecular weight 668.54 (C38H32BrF2NO3); MS (ESI): 668.1 (MH+).

b) 1-[4'-(4-{1-4-Fluorophenyl)-3-[3-(4-fluorophenyl)-3-hydroxypropyl]-4-oxoazetidin-2-yl}phenoxymethyl)biphenyl-4-ylmethyl]-4-aza-1-azoniabicyclo[2.2.2]octane bromide (22)

Compound (21) and DABCO were dissolved in toluene and reacted analogously to Example IV, giving the product (22) as a colorless solid of molecular weight 780.76 (C44H44BrF2N3O3); MS (ESI): 700.3 (MH+).

EXAMPLE XI 1-(4-Fluorophenyl)-3-[3-(4-fluorophenyl)-3-hydroxypropyl]-4-(4-{4'-[(2,3,4,5,6-pentahydroxyhexylamine)-methyl]-biphenyl-4-ylmethoxy}-phenyl)-azetidin-2-one (23)

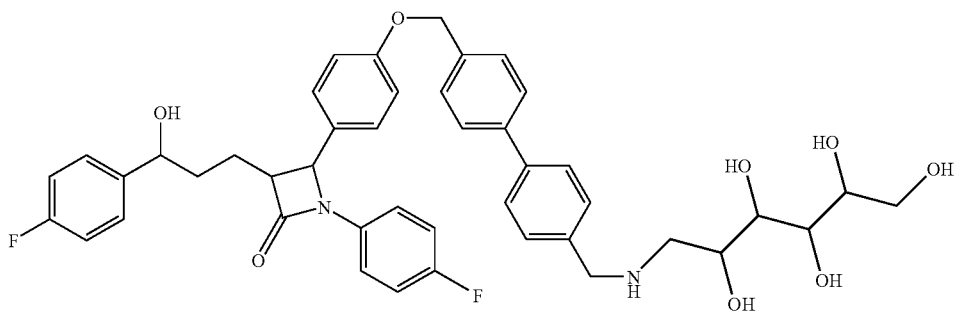

Compound (21) and glucamine were dissolved in dimethylformamide and reacted analogously to Example V, giving the product (23) as a colorless solid of molecular weight 768.86 (C44H46F2N2O8); MS (ESI): 769.3 (MH+).

EXAMPLE XII 1-(4-{4-[3-[3-(4-Fluorophenyl)-3-hydroxypropyl]-2-(4-methoxyphenyl)-4-oxoazetidin-1-yl]-phenoxymethyl}-benzyl)-4-aza-1-azoniabicyclo[2.2.2]octane bromide (26)

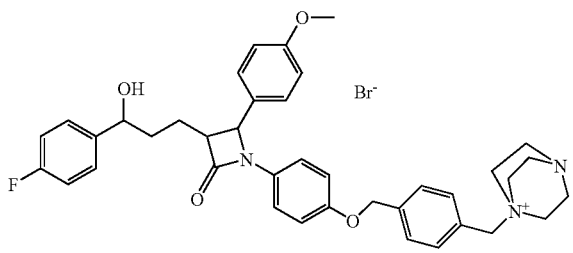

a) 3-[3-(4-Fluorophenyl)-3-hydroxypropyl]-1-(4-hydroxyphenyl)-4-(4-methoxyphenyl)-azetidin-2-one (24)

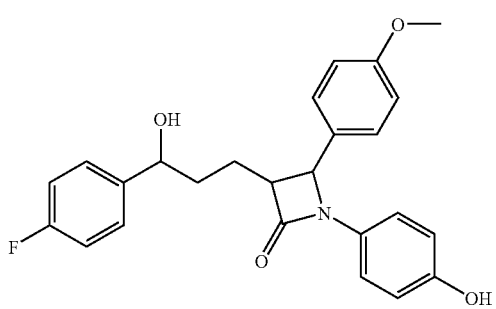

This compound was prepared as described above for 1-(4-aminomethylphenyl)-3-[3-(4-fluorophenyl)-3-hydroxypropyl]-4-(4-methoxyphenyl)-azetidin-2-one (steps a, b, c, and d), except that 4-[(4-methoxybenzylidene)-amino]-phenol was used. This produced 3-[3-(4-fluorophenyl)-3-hydroxypropyl]-1-(4-hydroxyphenyl)-4-(4-methoxyphenyl)-azetidin-2-one (24) of molecular weight 421.47 (C25H24FNO4); MS (ESI): 422.2 (MH+).

b) 1-[4-(4-bromomethylbenzyloxy)-phenyl]-3-[3-(4-fluorophenyl)-3-hydroxypropyl]4-(4-methoxyphenyl)-azetidin-2-one (25)

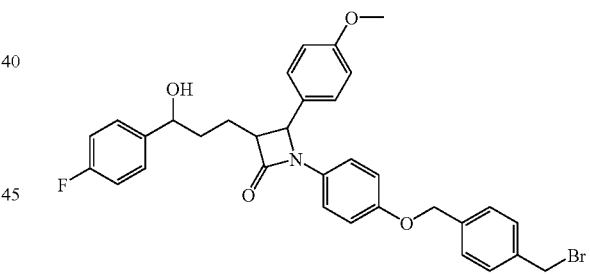

3-[3-(4-Fluorophenyl)-3-hydroxypropyl]-1-(4-hydroxyphenyl)-4-(4-methoxyphenyl)-azetidin-2-one was reacted with 1,4-bisbromomethylbenzene and potassium carbonate analogously to Example IV, giving a colorless solid (25) of molecular weight 604.52 (C33H31 BrFNO4); MS (ESI): 605.2 (MH+).

c) 1-(4-{4-[3-[3-(4-Fluorophenyl)-3-hydroxypropyl]-2-(4-methoxyphenyl)-4-oxoazetidin-1-yl]-phenoxymethyl}-benzyl)-4-aza-1-azoniabicyclo[2.2.2] octane bromide (26)

Compound (25) and DABCO were dissolved in toluene and reacted analogously to Example IV, giving the product (26) as a colorless solid of molecular weight 716.70 (C39H43BrFN3O4); MS (ESI): 636.3 (MH+).

EXAMPLE XIII

3-[3-(4-Fluorophenyl)-3-hydroxypropyl]-4-(4-methoxyphenyl)-1-(4-{4-[(2,3,4,5,6-pentahydroxyhexylamine)-methyl]-benzyloxy}-phenyl)-azetidin-2-one (27)

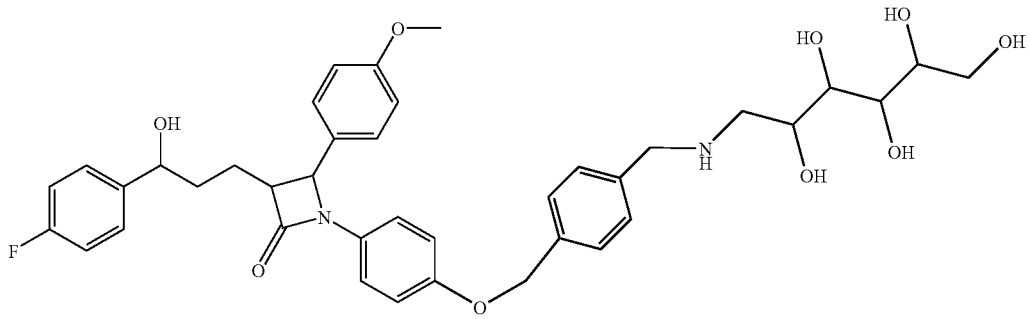

Compound (25) and glucamine were dissolved in dimethylformamide and reacted analogously to Example V, giving the product (27) as a colorless solid of molecular weight 704.80 (C39H45FN2O9); MS (ESI): 705.31 (MH+).

EXAMPLE XIV

1-[4-(4-{3-[1-(4-Fluorophenyl)-2-(4-methoxyphenyl)-4-oxoazetidin-3-yl]-1-hydroxypropyl}-phenoxymethyl)-benzyl]-4-aza-1-azoniabicyclo[2.2.2]octane bromide (30)

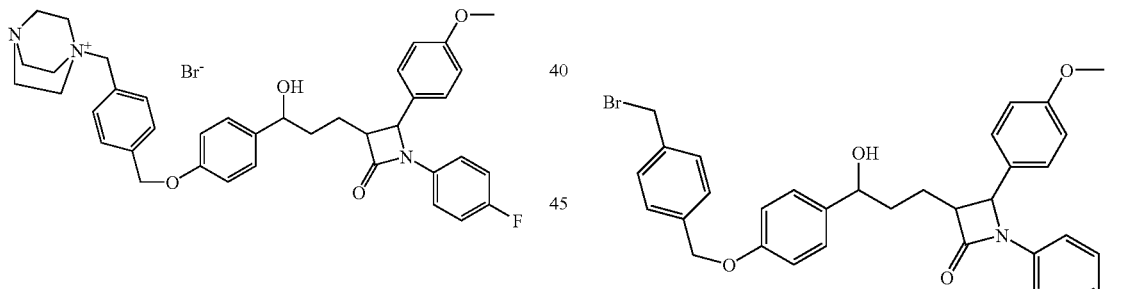

a) 1-(4-Fluorophenyl)-3-[3-hydroxy-3-(4-hydroxyphenyl)-propyl]-4-(4-methoxyphenyl)-azetidin-2-one (28)

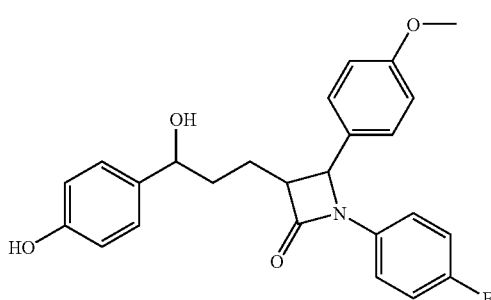

This compound was prepared as described above for 1-(4-aminomethylphenyl)-3-[3-(4-fluorophenyl)-3-hydroxypropyl]-4-(4-methoxyphenyl)-azetidin-2-one, except that 3-[5-(4-hydroxyphenyl)-5-hydroxypentanoyl]4-phenyloxazolidin-2-one and (4-fluorophenyl)-(4-methoxybenzylidene)-amine were used. This produced 1-(4-fluorophenyl)-3-[3-hydroxy-3-(4-hydroxyphenyl)-propyl]-4-(4-methoxyphenyl)-azetidin-2-one (28) of molecular weight 421.47 (C25H24FNO4); MS (ESI): 422.2 (MH+).

b) 3-{3-[4-(4-Bromomethylbenzyloxy)-phenyl]-3-hydroxypropyl}-1-(4-fluorophenyl)4-(4-methoxyphenyl)-azetidin-2-one (29)

1-(4-Fluorophenyl)-3-[3-hydroxy-3-(4-hydroxyphenyl)-propyl]-4-(4-methoxyphenyl)-azetidin-2-one was reacted with 1,4-bisbromomethylbenzene and potassium carbonate analogously to Example IV, giving a colorless solid (29) of molecular weight 604.52 (C33H31BrFNO4); MS (ESI): 605.2 (MH+).

c) 1-[4-(4-{3-[1-(4-Fluorophenyl)-2-(4-methoxyphenyl)-4-oxoazetidin-3-yl]-1-hydroxypropyl}-phenoxymethyl)-benzyl]-4-aza-1-azoniabicyclo[2.2.2]octane bromide (30)

Compound (29) and DABCO were dissolved in toluene and reacted analogously to Example IV, giving the product (30) as a colorless solid of molecular weight 716.70 (C39H43BrFN3O4); MS (ESI): 636.3 (MH+).

EXAMPLE XV

1-{4-[(4-{1-(4-Fluorophenyl)-3-[3-(4-fluorophenyl)-3-hydroxypropyl]-4-oxoazetidin-2-yl}-benzylcarbamoyl)-methyl]-benzyl}4-aza-1-azoniabicyclo[2.2.2]octane trifluoroacetate (35)

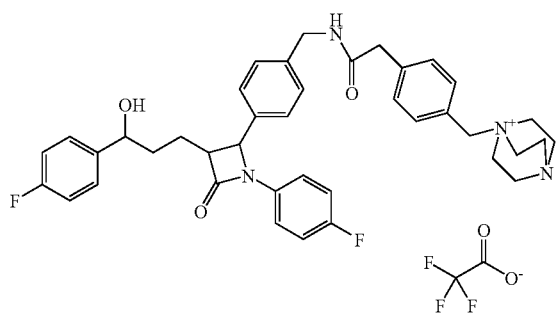

a) 1-(4-Carboxymethylbenzyl)-4-aza-1-azoniabicyclo[2.2.2]octane bromide (31)

At 70° C., 1.0 g of (3-bromomethylphenyl) acetic acid in 5 ml of dimethyl sulfoxide were added to a solution of 1.5 g of 1,4-diazabicyclo[2.2.2]octane in 10 ml of dimethyl sulfoxide. After 1 h, 100 ml of water were added and the mixture was freeze-dried. The residue was digested with acetone. The residue contained the product of molecular weight 261.35 (cation: C15H21 N2O2+); MS (ESI) 261.1 (M+).

b) 4-[5-(4-Fluorophenyl)-1-(4-fluorophenylamino)-5-hydroxy-2-(2-oxo-4-phenyloxazolidine-3-carbonyl)-pentyl]-benzonitrile (32)

Under argon, 2.5 g of 3-[5-(4-fluorophenyl)-5-hydroxy-pentanoyl]-4-phenyloxazolidin-2-one were dissolved in 30 ml of dichloromethane. 3.9 g of 4-[(4-fluorophenylimino)-methyl]-benzonitrile were added and the mixture was cooled to −10° C. 6.4 ml of diisopropylethylamine and, over a period of 30 min, 4.05 ml of trimethylsilyl chloride were added to this mixture so that the temperature did not exceed −5° C. The mixture was stirred at this temperature for 1 additional hour and then cooled to −25° C. 0.8 ml of titanium tetrachloride were then added slowly. The dark mixture was stirred at a temperature ranging from −25 to −30° C. overnight and then decomposed using 35 ml of a 7 percent strength solution of tartaric acid. The solution was then stirred at room temperature for another hour. 15 ml of a 20 percent strength solution of sodium bicarbonate were then added, and the mixture was again stirred for 1 hour. Following phase separation, the organic phase was washed with 30 ml of water, dried over magnesium sulfate and concentrated to about 10 ml. Following the addition of 2 ml of bistrimethylsilylacetamide, the mixture was heated at reflux for 30 min and then concentrated under reduced pressure. The residue was crystallized using ethyl acetate/heptane. The product was filtered off with suction and dried under reduced pressure. This gave the product of molecular weight 653.81 (C37H37F2N3O4Si); MS (ESI+): 654.3 (M+H+), 582.2 (M+H+-Si(CH3)3).

c) {1-(4-Fluorophenyl)-3-[3-(4-fluorophenyl)-3-hydroxypropyl]-4-oxoazetidin-2-yl}-benzonitrile (33)

2 g of 4-[5-(4-Fluorophenyl)-1-(4-fluorophenylamino)-5-hydroxy-2-(2-oxo-4-phenyl-oxazolidine-3-carbonyl)-pentyl]-benzonitrile were dissolved in 20 ml of methyl-tert-butyl ether and, together with 100 mg of tetrabutylammonium fluoride trihydrate and 1.3 ml of bistrimethylsilyl acetamide, heated at 40° C. for about 1 h. The reaction was monitored by thin-layer chromatography. After the reaction ended, 0.2 ml of glacial acetic acid were initially added and the mixture was stirred for 30 min and then concentrated. 20 ml of a mixture of isopropanol/2N sulfuric acid=10:1 were added to the residue, and the mixture was stirred for 1 hour. Following addition of a spatula tip of solid sodium bicarbonate, the mixture was again concentrated under reduced pressure. The residue was taken up in ethyl acetate and the organic phase was washed with water and dried. The residue was, after removal of the solvent, purified by column chromatography (SiO2, CH2Cl2/methanol=100:1). This gave the product of molecular weight 418.45 (C25H20F2N2O2); MS (DCl+): 419 (M+H+).

d) 4-(4-Aminomethylphenyl)-1-(4-fluorophenyl)-3-[3-(4-fluorophenyl)-3-hydroxypropyl]-azetidin-2-one (34)

200 mg of {1-(4-fluorophenyl)-3-[3-(4-fluorophenyl)-3-hydroxypropyl]-4-oxoazetidin-2-yl}-benzonitrile were dissolved in 20 ml of ethanol and, with 0.5 ml of conc. ammonia, hydrogenated over Raney nickel at a hydrogen pressure of 75 bar and at 25° C. for 30 hours. The catalyst was filtered off with suction, the mixture was concentrated under reduced pressure and the residue was purified by column filtration (SiO$_2$, CH$_2$Cl$_2$/methanol/conc. NH$_3$=100:10:1). This gives the product of molecular weight 422.5 (C25H22F2N2O2); MS (DCl+): 423 (M+H+), 405 (M+H+-H2O).

e) 1-{4-[(4-{1-(4-Fluorophenyl)-3-[3-(4-fluorophenyl)-3-hydroxypropyl]-4-oxoazetidin-2-yl}-benzylcarbamoyl)-methyl]-benzyl}-4-aza-1-azonia-bicyclo[2.2.2]octane; trifluoroacetate (35)

A solution of 70 mg 4-(4-aminomethylphenyl)-1-(4-fluorophenyl)-3-[3-(4-fluorophenyl)-3-hydroxypropyl]-azetidin-2-one, and 23 µl of triethylamine in 0.5 ml of dimethylformamide were added to a solution of 84 mg of 1-(4-carboxymethylbenzyl)-4-aza-1-azoniabicyclo[2.2.2]octane bromide, 64 µl of diisopropylcarbodiimide and 56 mg of hydroxybenzotriazole in 2 ml of dimethylformamide. The mixture was stirred at room temperature for 12 h. The reaction solution was concentrated and separated by HPLC (Knauer Eurospher-100-10-C18, water (0.1% trifluoroacetic acid)/acetonitrile (0.1% trifluoroacetic acid)=80/20→10/90). This gave the product of molecular weight 665.81 (cation: C40H43F2N4O3); MS (ESI) 665.33 (M+).

EXAMPLE XVI

1-{4-[(4-{1-(4-Fluorophenyl)-3-[3-(4-fluorophenyl)-3-hydroxypropyl]-4-oxoazetidin-2-yl}-benzylcarbamoyl)-methyl]-benzyl}-1-azoniabicyclo[2.2.2]octane trifluoroacetate (37)

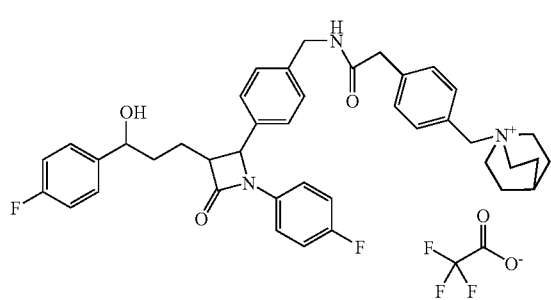

a) 1-(4-Carboxymethylbenzyl)-1-azoniabicyclo[2.2.2]octane bromide (36)

The synthesis was carried out analogously to Example XVa), starting with 1.67 g of 1-azabicyclo[2.2.2]octane. This gave the product of molecular weight 260.36 (cation: C16H22N1O2+); MS (ESI) 260.1 (M+).

b) 1-{4-[(4-{1-(4-Fluorophenyl)-3-[3-(4-fluorophenyl)-3-hydroxypropyl]-4-oxoazetidin-2-yl}-benzylcarbamoyl)-methyl]-benzyl}-1-azoniabicyclo[2.2.2]octane trifluoroacetate (37)

The synthesis was carried out analogously to Example XVe), starting with 70 mg of 4-(4-aminomethylphenyl)-1-(4-fluorophenyl)-3-[3-(4-fluorophenyl)-3-hydroxypropyl]-azetidin-2-one and 85 mg of 1-(4-carboxymethylbenzyl)-1-azoniabicyclo[2.2.2]octane bromide. This gave the product of molecular weight 664.82 (cation: C41H44F2N3O3+); MS (ESI) 664.33 (M+).

EXAMPLE XVII

1-{4-[(4-{1-(4-Fluorophenyl)-3-[3-(4-fluorophenyl)-3-hydroxypropyl]-4-oxoazetidin-2-yl}-benzylcarbamoyl)-methyl]-benzyl}-1,4-dimethylpiperazin-1-ium trifluoroacetate (39)

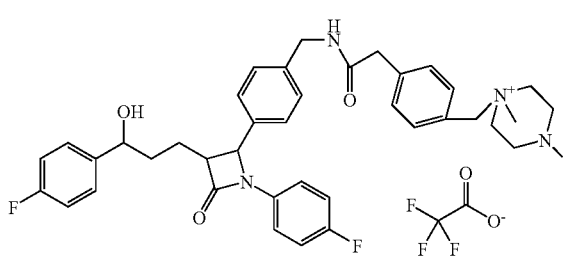

a) 1-(4-Carboxymethyl benzyl)-1,4-dimethylpiperazin-1-ium bromide (38)

The synthesis was carried out analogously to Example XVa), starting with 1.02 ml of 1,4-dimethylpiperazine. This gave the product of molecular weight 263.36 (cation: C15H23N2O2+); MS (ESI) 263.1 (M+).

b) 1-{4-[(4-{1-(4-Fluorophenyl)-3-[3-(4-fluorophenyl)-3-hydroxypropyl]-4-oxoazetidin-2-yl}-benzylcarbamoyl)-methyl]-benzyl}-1,4-dimethyl-piperazin-1-ium trifluoroacetate (39)

The synthesis was carried out analogously to Example XVe), starting with 70 mg of 4-(4-aminomethylphenyl)-1-(4-fluorophenyl)-3-[3-(4-fluorophenyl)-3-hydroxypropyl]-azetidin-2-one and 86 mg of 1-(4-carboxymethylbenzyl)-1,4-dimethylpiperazin-1-ium bromide. This gave the product of molecular weight 667.82 (cation: C40H45F2N4O3+); MS (ESI) 667.34 (M+).

EXAMPLE XVIII

4-{4-[(4-{1-(4-Fluorophenyl)-3-[3-(4-fluorophenyl)-3-hydroxypropyl]-4-oxoazetidin-2-yl}-benzylcarbamoyl)-methyl]-benzyl}-4-methylmorpholin-4-ium trifluoroacetate (41)

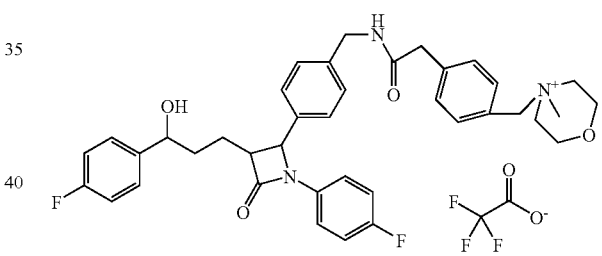

a) 4-(4-Carboxymethylbenzyl)-4-methylmorpholin-4-ium bromide (40)

The synthesis was carried out analogously to Example XVa), starting with 1.65 ml of N-methylmorpholine. This gave the product of molecular weight 250.32 (cation: C14H20N1O3+); MS (ESI) 250.1 (M+).

b) 4-{4-[(4-{1-(4-Fluorophenyl)-3-[3-(4-fluorophenyl)-3-hydroxypropyl]-4-oxoazetidin-2-yl}-benzylcarbamoyl)-methyl]-benzyl}-4-methylmorpholin-4-ium trifluoroacetate (41)

The synthesis was carried out analogously to Example XVe), starting with 70 mg of 4-(4-aminomethylphenyl)-1-(4-fluorophenyl)-3-[3-(4-fluorophenyl)-3-hydroxypropyl]-azetidin-2-one and 82 mg of 4-(4-carboxymethylbenzyl)-4-methylmorpholin-4-ium bromide. This gave the product of molecular weight 654.78 (cation: C39H42F2N3O4+); MS (ESI) 654.31 (M+).

EXAMPLE XIX

1-{4-[(4-{1-(4-Fluorophenyl)-3-[3-(4-fluorophenyl)-3-hydroxypropyl]-4-oxoazetidin-2-yl}-benzylcarbamoyl)-methyl]-benzyl}-1,4,7-trimethyl-[1,4,7]triazonan-1-ium trifluoroacetate (43)

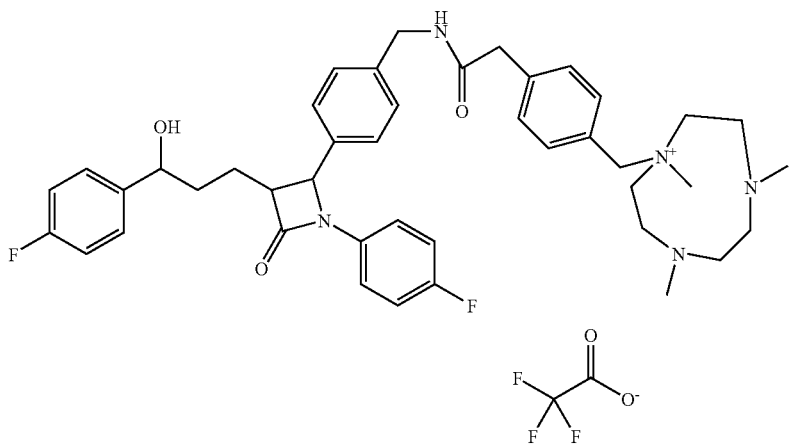

a) 1,4,7-Trimethyl-1-[4-(2-oxopropyl)-benzyl]-[1,4,7]triazonan-1-ium bromide (42)

The synthesis was carried out analogously to Example XVa), starting with 500 mg of 1,4,7-trimethyl-[1,4,7]triazonane. This gave the product of molecular weight 321.47 (cation: C18H31N3O2+); MS (ESI) 321.2 (M+).

b) 1-{4-[(4-{1-(4-Fluorophenyl)-3-[3-(4-fluorophenyl)-3-hydroxypropyl]-4-oxoazetidin-2-yl}-benzylcarbamoyl)-methyl]-benzyl}-1,4,7-trimethyl-[1,4,7]triazonan-1-ium trifluoroacetate (43)

The synthesis was carried out analogously to Example XVe) starting with 70 mg of 4-(4-aminomethylphenyl)-1-(4-fluorophenyl)-3-[3-(4-fluorophenyl)-3-hydroxypropyl]-azetidin-2-one and 200 mg of 1,4,7-trimethyl-1-[4-(2-oxopropyl)-benzyl]-[1,4,7]triazonan-1-ium bromide. This gave the product of molecular weight 724.92 (cation: C40H45F2N4O3+); MS (ESI) 724.40 (M+).

EXAMPLE XX

1-[4-({4-[3-(3-Hydroxy-3-phenylpropyl)-2-oxo4-phenylazetidin-1-yl]-benzylcarbamoyl}-methyl)-benzyl]-4-aza-1-azoniabicyclo[2.2.2]octane trifluoroacetate (44)

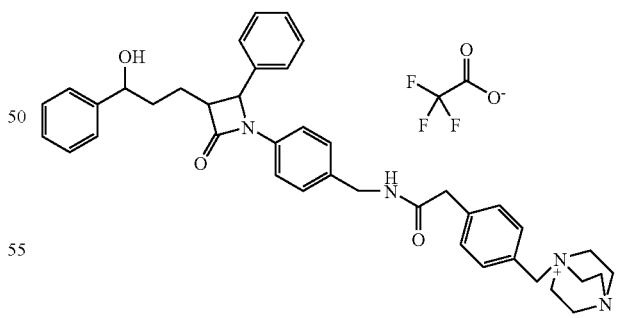

The synthesis was carried out analogously to Example XVe), starting with 60 mg of 1-(4-aminomethylphenyl)-3-(3-hydroxy-3-phenylpropyl)-4-phenylazetidin-2-one (8) and 82 mg of 1-(4-carboxymethylbenzyl)-4-aza-1-azoniabicyclo[2.2.2]octane bromide. This gave the product of molecular weight 629.83 (cation: C40H45F2N4O3+); MS (ESI) 629.35 (M+).

EXAMPLE XXI

N-(4-{1-(4-Fluorophenyl)-3-[3-(4-fluorophenyl)-3-hydroxypropyl]-4-oxoazetidin-2-yl}-benzyl)-2-{4-[(2,3,4,5,6-pentahydroxyhexylamino)-methyl]-phenyl}-acetamide (46)

EXAMPLE XXII

N-(4-{1-(4-Fluorophenyl)-3-[3-(4-fluorophenyl)-3-hydroxypropyl]-4-oxoazetidin-2-yl}-benzyl)-2-4-{[methyl-(2,3,4,5,6-pentahydroxyhexyl)-amino]-methyl}-phenyl)-acetamide (48)

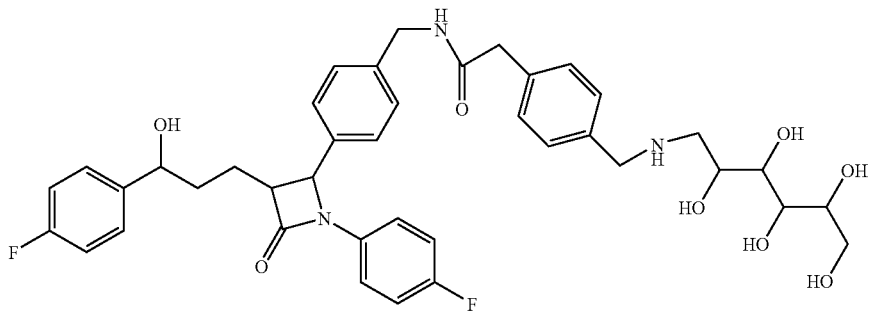

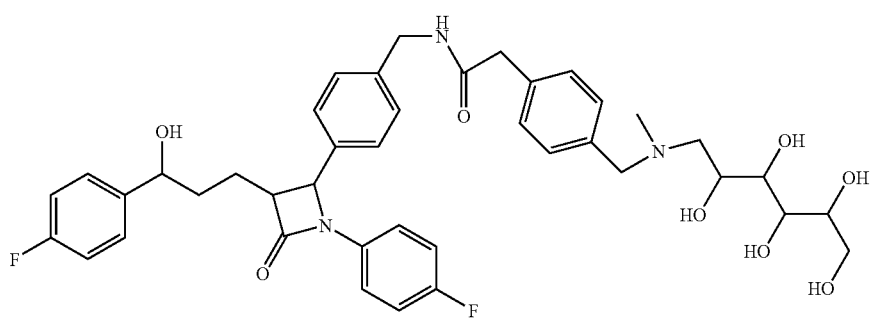

a) {4-[(2,3,4,5,6-Pentahydroxyhexylamino)-methyl]-phenyl}-acetic acid (45)

The synthesis was carried out analogously to Example XVa), starting with 989 mg of 6-aminohexane-1,2,3,4,5-pentaol. This gave the product of molecular weight 329.35 (C15H23N1O7); MS (ESI) 330.2 (M+H+).

b) N-(4-{1-(4-Fluorophenyl)-3-[3-(4-fluorophenyl)-3-hydroxypropyl]-4-oxoazetidin-2-yl}-benzyl)-2-{4-[(2,3,4,5,6-pentahydroxyhexylamino)-methyl]-phenyl}-acetamide (46)

The synthesis was carried out analogously to Example XVe), starting [lacuna] 70 mg of 4-(4-aminomethylphenyl)-1-(4-fluorophenyl)-3-[3-(4-fluorophenyl)-3-hydroxypropyl]-azetidin-2-one and 110 mg of {4-[(2,3,4,5,6-pentahydroxyhexylamino)-methyl]-phenyl}-acetic acid. This gave the product of molecular weight 733.82 (C40H45F2N3O8+); MS (ESI) 734.32 (M+H+).

a) (4-{[Methyl-(2,3,4,5,6-pentahydroxyhexyl)-amino]-methyl}-phenyl)-acetic acid (47)

The synthesis was carried out analogously to Example XVa), starting with 1.06 g of 6-methylaminohexane-1,2,3,4,5-pentaol. This gave the product of molecular weight 343.38 (C16H25N1O7); MS (ESI) 344.2 (M+H+).

b) N-(4-{1-(4-Fluorophenyl)-3-[3-(4-fluorophenyl)-3-hydroxypropyl]-4-oxoazetidin-2-yl}-benzyl)-2-(4-{[methyl-(2,3,4,5,6-pentahydroxyhexyl)-amino]-methyl}-phenyl)-acetamide (48)

The synthesis was carried out analogously to Example XVe), starting with 70 mg of 4-(4-aminomethylphenyl)-1-(4-fluorophenyl)-3-[3-(4-fluorophenyl)-3-hydroxypropyl]-azetidin-2-one and 114 mg of (4-{[methyl-(2,3,4,5,6-pentahydroxyhexyl)-amino]-methyl}-phenyl)-acetic acid. This gave the product of molecular weight 747.84 (C41H47F2N3O8+); MS (ESI) 748.35 (M+H+).

TABLE 1

Compounds of the formula I

| Ex. | R1, R2 | R3, R4 | R5, R6 | Salz | Molecular weight of the free base or acid (calculated) | Molecular weight (found) |
|---|---|---|---|---|---|---|
| XXIII | para | para-F, H | para-F, H | Cl⁻ | 651.78 | 651.31 (M⁺) |
| XXIV | para | para-F, H | para-F, H | CF₃COO⁻ | 651.78 | 651.31 (M⁺) |

TABLE 1-continued
Compounds of the formula I
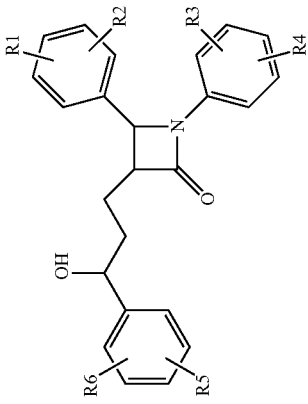
| Ex. | R1, R2 | R3, R4 | R5, R6 | Salz | Molecular weight of the free base or acid (calculated) | Molecular weight (found) |
|---|---|---|---|---|---|---|
| XXV | para, (trans-4-carboxycyclohexyl)-C(O)NH-ethyl, H | para-F, H | para-F, H | — | 567.64 | 577.25 (MH+) |
| XXVI | para, 4-(4-carboxyphenoxy)phenyl-C(O)NH-ethyl; OH, H | para-F, H | para-F, H | — | 662.69 | 663.22 (MH+) |
| XXVII | para-O—CH₃, H | para, 4-(CH₂C(O)NH-CH₂-(polyol))phenyl; OH, H | para-F, H | CF₃COOH | 745.85 | 746.34 (MH+) |

TABLE 1-continued
Compounds of the formula I
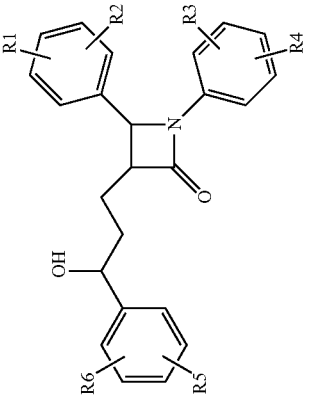
| Ex. | R1, R2 | R3, R4 | R5, R6 | Salz | Molecular weight of the free base or acid (calculated) | Molecular weight (found) |
|---|---|---|---|---|---|---|
| XXVIII | para-O—CH$_3$, H | 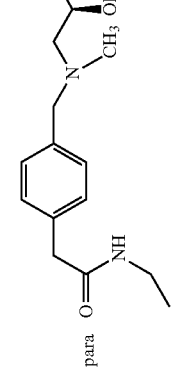 para | para-F, H | CF$_3$COOH | 759.88 | 760.35 (MH$^+$) |
| XXIX | para | 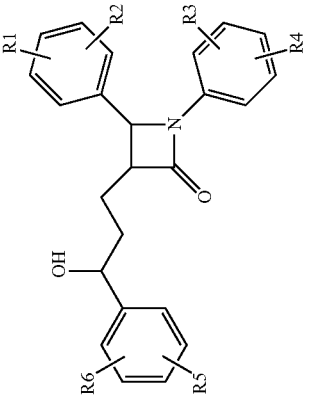 para-F, H | para-F, H | — | 739.82 | 740.33 (MH$^+$) |

TABLE 1-continued
Compounds of the formula I
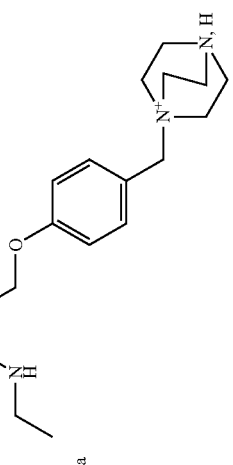
| Ex. | R1, R2 | R3, R4 | R5, R6 | Salz | Molecular weight of the free base or acid (calculated) | Molecular weight (found) |
|---|---|---|---|---|---|---|
| XXX | para 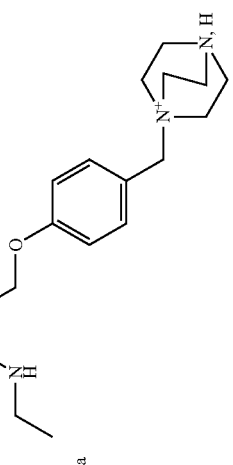 | para-F, H | para-F, H | CF$_3$COO$^-$ | 695.84 | 659.34 (M$^+$) |

TABLE 1-continued

Compounds of the formula I

| Ex. | R1, R2 | R3, R4 | R5, R6 | Salz | Molecular weight of the free base or acid (calculated) | Molecular weight (found) |
|---|---|---|---|---|---|---|
| XXXI | para | para-F, H | para-F, H | CF₃COO⁻ | 709.86 | 709.35 (M⁺) |
| XXXII | para | para-F, H | para-F, H | — | 614.60 | 597.18 (MH⁺ − H₂O) |

TABLE 1-continued
Compounds of the formula I
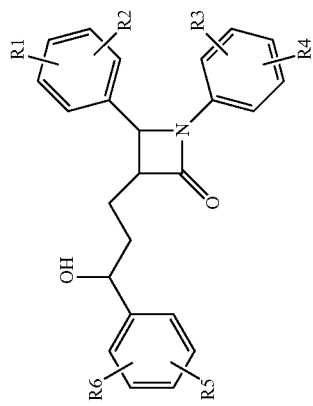
| Ex. | R1, R2 | R3, R4 | R5, R6 | Salz | Molecular weight of the free base or acid (calculated) | Molecular weight (found) |
|---|---|---|---|---|---|---|
| XXXIII | para 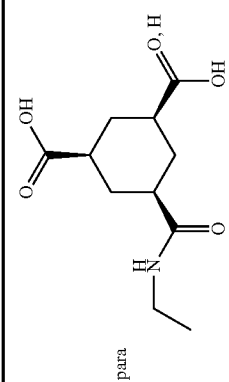 | para-F, H | para-F, H | — | 620.65 | 621.24 (MH⁺) |
| XXXIV | para 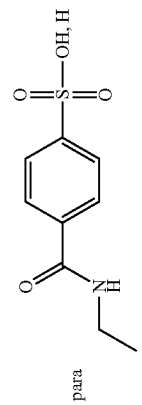 | para-F, H | para-F, H | — | 606.65 | 607.32 (MH⁺) |

TABLE 1-continued

Compounds of the formula I

| Ex. | R1, R2 | R3, R4 | R5, R6 | Salz | Molecular weight of the free base or acid (calculated) | Molecular weight (found) |
|---|---|---|---|---|---|---|
| XXXV | para | para-F, H | para-F, H | CF₃COO⁻ | 681.33 | 681.5 (M⁺) |
| XXXVI | para-O—CH₃, H | para | para-F, H | Cl⁻ | 755.92 | 755.36 (M⁺) |
| XXXVII | para-O—CH₃, H | para | H, H | — | 615.71 | 616.21 (MH⁺) |

TABLE 1-continued
Compounds of the formula I
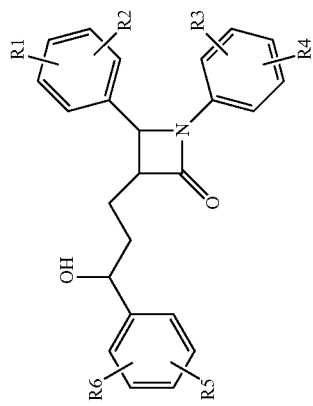
| Ex. | R1, R2 | R3, R4 | R5, R6 | Salz | Molecular weight of the free base or acid (calculated) | Molecular weight (found) |
|---|---|---|---|---|---|---|
| XXXVIII | para 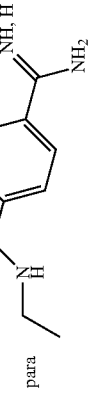 | para-F, H | para-F, H | CF₃COOH | 554.65 | 555.20 (MH⁺) |
| XXXIX | para 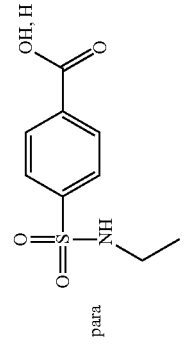 | para-F, H | para-F, H | — | 606.65 | 607.39 (MH⁺) |

TABLE 1-continued
Compounds of the formula I
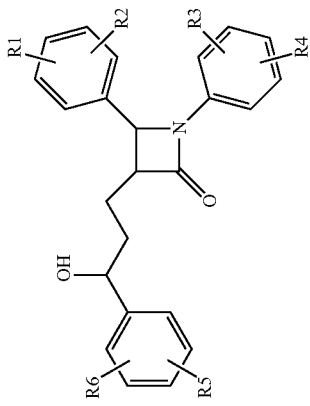
| Ex. | R1, R2 | R3, R4 | R5, R6 | Salz | Molecular weight of the free base or acid (calculated) | Molecular weight (found) |
|---|---|---|---|---|---|---|
| XL | para-O—CH$_3$, H | 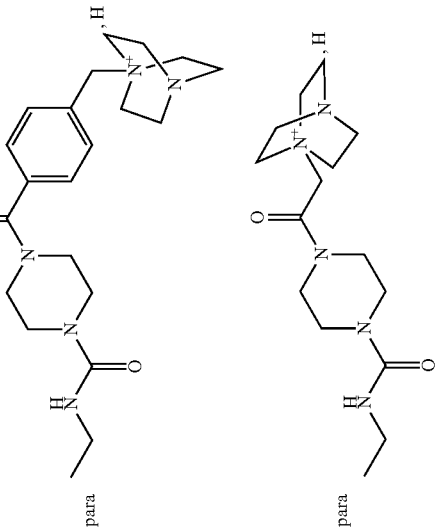 para | para-F, H | Cl$^-$ | 775.95 | 775.40 (M$^+$) |
| XLI | para-O—CH$_3$, H | para | para-F, H | Cl$^-$ | 699.85 | 699.33 (M$^+$) |

TABLE 1-continued

Compounds of the formula I

| Ex. | R1, R2 | R3, R4 | R5, R6 | Salz | Molecular weight of the free base or acid (calculated) | Molecular weight (found) |
|---|---|---|---|---|---|---|
| XLII | para-O—CH₃, H | *(4-amidinophenyl-NH-C(O)-CH₂-CH₂-C(O)-NH-, para)* | para-F, H | HCl | 651.74 | 652.38 (MH⁺) |
| XLIII | para-O—CH₃, H | *(quinuclidinium-CH₂-phenyl-C(O)-NH-pentyl, para)* | para-F, H | Br⁻ | 860.51 | 860.6 (M⁺) |

TABLE 1-continued

Compounds of the formula I

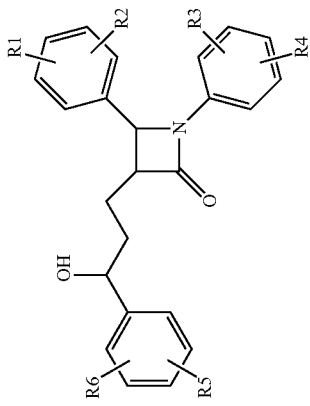

| Ex. | R1, R2 | R3, R4 | R5, R6 | Salz | Molecular weight of the free base or acid (calculated) | Molecular weight (found) |
|---|---|---|---|---|---|---|
| XLIV | para-O—CH$_3$, H | ![para structure with NH, NH$_2$, H] para | para-F, H | — | 595.67 | 596.38 (MH$^+$) |
| XLV | para-O—CH$_3$, H | ![para structure with NH$_2$, H] para | para-F, H | CF$_3$COOH | 652.73 | 653.37 (MH$^+$) |
| XLVI | para-O—CH$_3$, H | ![para structure with OH, H sulfonic] para | para-F, H | — | 618.68 | 617.33 (M-H$^+$; measured in negative mode |

TABLE 1-continued

Compounds of the formula I

| Ex. | R1, R2 | R3, R4 | R5, R6 | Salz | Molecular weight of the free base or acid (calculated) | Molecular weight (found) |
|---|---|---|---|---|---|---|
| XLVII | para-O—CH₃, H | para, (4-sulfophenyl)carbonyl-piperazine-N-ethylcarboxamide | para-F, H | — | 730.81 | 731.41 (MH⁺) |
| XLVIII | para-O—CH₃, H | para, 4-(4-carboxybenzyl)-N-ethylbenzamide | para-F, H | — | 672.76 | 655.28 (MH⁺ − H₂O) |

TABLE 1-continued
Compounds of the formula I
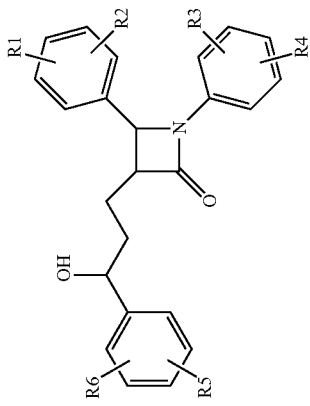
| Ex. | R1, R2 | R3, R4 | R5, R6 | Salz | Molecular weight of the free base or acid (calculated) | Molecular weight (found) |
|---|---|---|---|---|---|---|
| IL | para-O—CH₃, H | para, (4-carboxybiphenyl-4-yl)-C(O)NH-ethyl | para-F, H | — | 658.73 | 659.27 (MH⁺) |
| L | para-O—CH₃, H | para, (4-(4-sulfophenoxy)phenyl)-C(O)NH-ethyl | para-F, H | — | 710.78 | 693.25 (MH⁺ − H₂O) |
| LI | para-O—CH₃, H | para, (4-(quinuclidinium-methyl)phenyl)-C(O)NH-ethyl | para-F, H | Cl⁻ | 663.82 | 663.28 (M⁺) |

TABLE 1-continued

Compounds of the formula I

| Ex. | R1, R2 | R3, R4 | R5, R6 | Salz | Molecular weight of the free base or acid (calculated) | Molecular weight (found) |
|---|---|---|---|---|---|---|
| LII | para-O—CH$_3$, H | para, [cyclohexane carboxylic acid amide structure] | para-F, H | — | 588.68 | 589.34 (MH$^+$) |
| LIII | para-O—CH$_3$, H | para, [phenoxy benzoic acid amide structure] | para-F, H | — | 674.73 | 657.35 (MH$^+$ − H$_2$O) |
| LIV | para-O—CH$_3$, H | para, [sulfonic acid phenylurea structure] | para-F, H | — | 633.70 | 615.70 (M$^+$ − H$_2$O) |

TABLE 1-continued

Compounds of the formula I

| Ex. | R1, R2 | R3, R4 | R5, R6 | Salz | Molecular weight of the free base or acid (calculated) | Molecular weight (found) |
|---|---|---|---|---|---|---|
| LV | para-O—CH₃, H | para | para-F, H | Br | 666.72 | 666.33 (M⁺) |
| LVI | para | para-F, H | para-F, H | Br | 654.68 | 654.31 (M⁺) |
| LVII | para | para-F, H | para-F, H | I⁻ | 687.35 | 687.4 (M⁺) |

TABLE 1-continued

Compounds of the formula I

| Ex. | R1, R2 | R3, R4 | R5, R6 | Salz | Molecular weight of the free base or acid (calculated) | Molecular weight (found) |
|---|---|---|---|---|---|---|
| LVIII | para- (4-ethylpiperazine-1-sulfonyl) | para-F, H | para-F, H | — | 571.65 | 572.4 (MH⁺) |
| LIX | para- (4-{[(ethylamino)carbonyl]amino}phenyl)sulfonyl | para-F, H | para-F, H | — | 621.66 | 622.33 (MH⁺) |
| LX | para-O—CH₃, H | para- (N-ethyl octanamide) | para-F, H | — | 801.98 | 784.21 (M⁺ − H₂O) |

TABLE 1-continued

Compounds of the formula I

| Ex. | R1, R2 | R3, R4 | R5, R6 | Salz | Molecular weight of the free base or acid (calculated) | Molecular weight (found) |
|---|---|---|---|---|---|---|
| LXI | para-O—CH₃, H | para (hexyl-urea-ethyl-C(O)NH-C₆H₄-SO₂-OH) | para-F, H | — | 775.90 | 758.18 (M⁺ − H₂O) |

TABLE 1-continued

Compounds of the formula I

| Ex. | R1, R2 | R3, R4 | R5, R6 | Salz | Molecular weight of the free base or acid (calculated) | Molecular weight (found) |
|---|---|---|---|---|---|---|
| LXII | para-O—CH₃, H | para | para-F, H | — | 882.04 | 883.49 (MH⁺) |

Using the methods described below, the activity of the compounds of the formula I according to the invention was examined:

Effect of the Compounds of the Invention on Cholesterol Absorption and 3H-Taurocholic Acid Excretion Using Fecal Excrement of Mice, Rats or Hamsters NMRI mice, Wistar rats, or Golden Syrian hamsters (in groups of n=4-6) were kept in metabolic cages, where they were fed with a standard diet (Altromin, Lage (Lippe)). The afternoon prior to the administration of the radioactive tracers (14C-cholesterol), the feed was removed and the animals were adapted to grates.

Additionally, the animals were labeled s.c. with 3H-TCA (taurocholic acid) (for example 1 µCi/mouse up to 5 µCi/rat) 24 hours prior to the peroral administration of the test meal (14C-cholesterol in Intralipid® 20, Pharmacia-Upjohn).

Cholesterol absorption test: 0.25 ml/mouse Intralipid® 20 (Pharmacia-Upjohn) ((spiked with 0.25 µCi of 14C-cholesterol in 0.1 mg of cholesterol) was administered perorally by gavage.

Test substances were prepared separately in 0.5% methylcellulose (Sigma)/5% Solutol (BASF, Ludwigshafen) or a suitable vehicle.

The administration volume of the test substance was 0.5 ml/mouse. The test substance was administered immediately prior to the test meal (Intralipid labeled with 14C-cholesterol) (cholesterol absorption test).

The feces were collected over a period of 24 h. Fecal elimination of 14C-cholesterol and 3H-taurocholic acid (TCA) was determined after 24 hours.

The livers were removed and homogenized, and aliquots were incinerated in an oximate (Model 307, Packard) to determine the amount of 14C-cholesterol that had been taken up/absorbed.

Evaluation

Feces Samples

The total weight was determined, the sample was made up with water to a defined volume and then homogenized, and an aliquot was evaporated to dryness and incinerated in an oximate (Model 307 from Packard for the incineration of radioactively labeled samples). Fhe amount of radioactive $^3H-H_2O$ and $^{14}C-CO_2$ was extrapolated to the amount of $^3H$-taurocholic acid and $^{14}C$-cholesterol, respectively, that was excreted (dual isotope technique). The $ED_{200}$ values were interpolated from a dose-effect curve as those doses at which the excretion of TCA or cholesterol was doubled, based on a control group treated at the same time.

Liver Samples

The amount of 14C-cholesterol taken up by the liver was based on the administered dose. The ED50 values were interpolated from a dose-effect curve as the dose at which the uptake of 14C-cholesterol by the liver was halved (50%), based on a control group.

The $ED_{50}$ values below demonstrate the activity of the compounds of the formula I according to the invention

| Example No. | $ED_{50}$ (liver) [mg/mouse] |
|---|---|
| I | <0.1 |
| II | <1.0 |
| IV | <0.1 |
| V | <0.1 |
| VI | 0.3 |
| VII | <1.0 |
| VIII | <1.0 |
| IX | <0.1 |
| XV | <1.0 |
| XXIII | 0.3 |
| XXV | 0.3 |
| XXVI | 0.1 |
| XXVII | 0.3 |
| XXIX | 0.3 |
| XXXI | 0.3 |
| XXXVI | 0.03 |
| XXXVII | 0.1 |
| XXXVIII | 0.1 |
| XLI | 0.03 |
| XLIII | 0.3 |
| XLIV | 0.3 |
| XLVI | 0.3 |
| XLVIII | 0.03 |
| L | 0.1 |
| LII | 0.3 |
| LIII | 0.03 |

As can be seen from the table, the compounds of the formula I have very good cholesterol-lowering action.

Bioabsorption

The bioabsorption of the compounds of the formula I was examined using the Caco cell model (A. R. Hilgers et al., Caco-2 cell monolayers as a model for drug transport across the intestinal mucosa, Pharm. Res. 1990, 7, 902).

From the measured data, it can be seen that the bioabsorption of the compounds of the formula I according to the invention was considerably lower than that of the compounds described in the prior art (reference structure):

Reference structure:

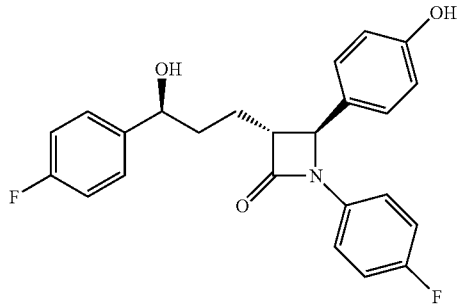

Ezetimibe

We claim:

1. A compound of the formula I,

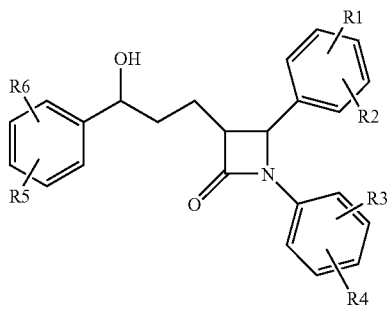

wherein:
R1, R2, R3, R4, R5, and R6, independently of one another, are chosen from:
$(C_1-C_{30})$-alkyl, wherein the $(C_1-C_{30})$-alkyl is substituted by q LAG units,
  wherein at least one carbon atom of the alkyl radical is replaced by:
    aryl or heteroaryl radicals, which are unsubstituted or substituted one, two, or three times by R7, or by $(C_3-C_{10})$-cycloalkyl or heterocycloalkyl radicals, which are unsubstituted or substituted one, two, three, or four times by R7, and
  wherein at least one carbon atom of the alkyl radical is optionally replaced by a radical chosen from: —S(O)$_m$—(where m=0-2), —O—, —(C=O)—, —(C=S)—, —CH=CH—, —C≡C—, —N(($C_1$-$C_6$)-alkyl)-, —N(phenyl)-, —N(($C_1$-$C_6$)-alkyl-phenyl)-, —N(CO—(CH$_2$)$_{1-10}$—COOH)— and —NH—; or
H, F, Cl, Br, I, CF$_3$, NO$_2$, N$_3$, CN, COOH, COO($C_1$-$C_6$)-alkyl, CONH$_2$, CONH($C_1$-$C_6$)-alkyl, CON[($C_1$-$C_6$)-alkyl]$_2$, ($C_1$-$C_6$)-alkyl, ($C_2$-$C_6$)-alkenyl, ($C_2$-$C_6$)-alkynyl, or O—($C_1$-$C_6$)-alkyl, wherein the alkyl radical is unsubstituted or at least one hydrogen in the alkyl radical is replaced by fluorine; or
SO$_2$—NH$_2$, SO$_2$NH($C_1$-$C_6$)-alkyl, SO$_2$N[($C_1$-$C_6$)-alkyl]$_2$, S—($C_1$-$C_6$)-alkyl, S—(CH$_2$)$_n$-phenyl, SO—($C_1$-$C_6$)-alkyl, SO—(CH$_2$)$_n$-phenyl, SO$_2$-($C_1$-$C_6$)-alkyl, or SO$_2$—(CH$_2$)$_n$-phenyl; wherein n=0-6, and wherein the phenyl radical is unsubstituted or substituted one or two times, each substituent chosen independently from: F, Cl, Br, OH, CF$_3$, NO$_2$, CN, OCF$_3$, O—($C_1$-$C_6$)-alkyl, ($C_1$-$C_6$)-alkyl, and NH$_2$; or
NH$_2$, NH—($C_1$-$C_6$)-alkyl, N(($C_1$-$C_6$)-alkyl)$_2$, NHCO($C_1$-$C_6$)-alkyl, phenyl, or O—(CH$_2$)$_n$-phenyl, wherein n=0-6, and wherein the phenyl ring is unsubstituted or substituted one, two, or three times, each substituent chosen independently from: F, Cl, Br, I, OH, CF$_3$, NO$_2$, CN, OCF$_3$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, COOH, COO—($C_1$-$C_6$)-alkyl, and CONH$_2$;
R7 represents F, Cl, Br, I, CF$_3$, NO$_2$, N$_3$, CN, COOH, COO($C_1$-$C_6$)-alkyl, CONH$_2$, CONH($C_1$-$C_6$)-alkyl, CON[($C_1$-$C_6$)-alkyl]$_2$, ($C_1$-$C_6$)-alkyl, ($C_2$-$C_6$)-alkenyl, ($C_2$-$C_6$)-alkynyl, or O—($C_1$-$C_6$)-alkyl, wherein the alkyl radical is unsubstituted or at least one hydrogen in the alkyl radical may be replaced by fluorine; or
PO$_3$H$_2$, SO$_3$H, SO$_2$—NH$_2$, SO$_2$NH($C_1$-$C_6$)-alkyl, SO$_2$N[($C_1$-$C_6$)-alkyl]$_2$, S—($C_1$-$C_6$)-alkyl, S—(CH$_2$)$_n$-phenyl, SO—($C_1$-$C_6$)-alkyl, SO—(CH$_2$)$_n$-phenyl, SO$_2$—($C_1$-$C_6$)-alkyl, or SO$_2$—(CH$_2$)$_n$-phenyl, wherein n=0-6, and wherein the phenyl radical is unsubstituted or substituted one or two times, each substituent chosen independently from: F, Cl, Br, OH, CF$_3$, NO$_2$, CN, OCF$_3$, O—($C_1$-$C_6$)-alkyl, ($C_1$-$C_6$)-alkyl, and NH$_2$; or
C(NH)(NH$_2$), NH$_2$, NH—($C_1$-$C_6$)-alkyl, N(($C_1$-$C_6$)-alkyl)$_2$, NHCO($C_1$-$C_6$)-alkyl, phenyl, or O—(CH$_2$)$_n$-phenyl, wherein n=0-6, and wherein the phenyl ring is unsubstituted or substituted one, two, or three times, each substituent chosen independently from: F, Cl, Br, I, OH, CF$_3$, NO$_2$, CN, OCF$_3$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, COOH, COO—($C_1$-$C_6$)-alkyl, and CONH$_2$;
(LAG) is an amino acid residue, or an oligopeptide residue comprising 2 to 9 amino acids;
wherein q=1-5;
and wherein at least one of the radicals R1 to R6 must have the meaning:
$(C_1-C_{30})$-alkyl, wherein the $(C_1-C_{30})$-alkyl is substituted by q LAG units,
  wherein at least one carbon atom of the alkyl radical is replaced by:
    aryl or heteroaryl radicals, which are unsubstituted or substituted one, two, or three times by R7, or
    ($C_3$-$C_{10}$)-cycloalkyl or heterocycloalkyl radicals, which are unsubstituted or substituted one, two, three, or four times by R7, or
    —S(O)$_m$—(where m=0-2), —O—, —(C=O)—, —(C=S)—, —CH=CH—, —C≡C—, —N(($C_1$-$C_6$)-alkyl)-, —N(phenyl)-, —N(($C_1$-$C_6$)-alkyl-phenyl)-, —N(CO—(CH$_2$)$_{1-10}$—COOH)— or —NH—;
or a pharmaceutically acceptable salt thereof, in any stereoisomeric form, or a mixture of any such compounds in any ratio.

2. A compound as claimed in claim 1, wherein
R2, R4, R5, and R6, independently of one another, are chosen from:
H, F, Cl, Br, I, CF$_3$, NO$_2$, N$_3$, CN, COOH, COO($C_1$-$C_6$)-alkyl, CONH$_2$, CONH($C_1$-$C_6$)-alkyl, CON[($C_1$-$C_6$)-alkyl]$_2$, ($C_1$-$C_6$)-alkyl, ($C_2$-$C_6$)-alkenyl, ($C_2$-$C_6$)-alkynyl, or O—($C_1$-$C_6$)-alkyl, wherein the alkyl radical is unsubstituted or at least one hydrogen in the alkyl radical is replaced by fluorine; or
SO$_2$—NH$_2$, SO$_2$NH($C_1$-$C_6$)-alkyl, SO$_2$N[($C_1$-$C_6$)-alkyl]$_2$, S—($C_1$-$C_6$)-alkyl, S—(CH$_2$)$_n$-phenyl, SO—($C_1$-$C_6$)-alkyl, SO—(CH$_2$)$_n$-phenyl, SO$_2$—($C_1$-$C_6$)-alkyl, or SO$_2$—(CH$_2$)$_n$-phenyl, wherein n=0-6, and wherein the phenyl radical is unsubstituted or substituted one or two times, each substituent chosen independently from: F, Cl, Br, OH, CF$_3$, NO$_2$, CN, OCF$_3$, O—($C_1$-$C_6$)-alkyl, ($C_1$-$C_6$)-alkyl, and NH$_2$; or
NH$_2$, NH—($C_1$-$C_6$)-alkyl, N(($C_1$-$C_6$)-alkyl)$_2$, NHCO($C_1$-$C_6$)-alkyl, phenyl, or O—(CH$_2$)$_n$-phenyl, wherein n=0-6, and wherein the phenyl ring is unsubstituted or substituted one, two, or three times, each substituent chosen independently from: F, Cl, Br, I, OH, CF$_3$, NO$_2$, CN, OCF$_3$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, COOH, COO—($C_1$-$C_6$)-alkyl, and CONH$_2$;
R1 and R3, independently of one another, are chosen from:
$(C_1-C_{30})$-alkylene-(LAG),
  wherein at least one carbon atom of the alkylene radical is replaced by:

aryl or heteroaryl radicals, which are unsubstituted or substituted one, two, or three times by R7, or by $(C_3-C_{10})$-cycloalkyl or heterocycloalkyl radicals, which are unsubstituted or substituted one, two, or three times by R7 and wherein at least one carbon atom of the alkylene radical is optionally replaced by a radical chosen from: $-S(O)_m-$ (where m=0-2), $-O-$, $-(C=O)-$, $-N(CH_3)-$, $-N(phenyl)-$, $-N(CO-(CH_2)_{1-10}-COOH)-$ and $-NH-$, or H, F, Cl, Br, I, $CF_3$, $NO_2$, $N_3$, CN, COOH, $COO(C_1-C_6)$-alkyl, $CONH_2$, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, or $O-(C_1-C_6)$-alkyl, wherein the alkyl radical is unsubstituted or at least one hydrogen in the alkyl radical is replaced by fluorine; or $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-phenyl, $SO-(C_1-C_6)$-alkyl, $SO-(CH_2)_n$-phenyl, $SO_2-(C_1-C_6)$-alkyl, or $SO_2-(CH_2)_n$-phenyl, wherein n=0-6, and wherein the phenyl radical is unsubstituted or substituted one or two times, each substituent chosen independently from: F, Cl, Br, OH, $CF_3$, $NO_2$, CN, $OCF_3$, $O-(C_1-C_6)$-alkyl, $(C_1-C_6)$-alkyl, and $NH_2$; or $NH_2$, $NH-(C_1-C_6)$-alkyl, $N((C_1-C_6)$-alkyl$)_2$, $NHCO(C_1-C_6)$-alkyl, phenyl, or $O-(CH_2)_n$-phenyl, wherein n=0-6, and wherein the phenyl ring is unsubstituted or substituted one, two, or three times, each substituent chosen independently from: F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SO_2-CH_3$, COOH, $COO-(C_1-C_6)$-alkyl, and $CONH_2$;

R7 represents F, Cl, Br, I, $CF_3$, $NO_2$, $N_3$, CN, COOH, $COO(C_1-C_6)$-alkyl, $CONH_2$, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, or $O-(C_1-C_6)$-alkyl, wherein the alkyl radical is unsubstituted or at least one hydrogen in the alkyl radical is replaced by fluorine; or $PO_3H_2$, $SO_3H$, $SO_2-NH_2$, $SO_2NH(C_1-C_6)$-alkyl, $SO_2N[(C_1-C_6)$-alkyl$]_2S-(C_1C_6)$-alkyl, $S-(CH_2)_n$-phenyl, $SO-(C_1-C_6)$-alkyl, $SO-(CH_2)$n-phenyl, $SO_2-(C_1-C_6)$-alkyl, or $SO_2-(CH_2)_n$-phenyl, wherein n=0-6, and wherein the phenyl radical is unsubstituted or substituted one or two times, each substituent chosen independently from: F, Cl, Br, OH, $CF_3$, $NO_2$, CN, $OCF_3$, $O-(C_1-C_6)$-alkyl, $(C_1-C_6)$-alkyl, and $NH_2$; or $C(NH)(NH_2)$, $NH_2$, $NH-(C_1-C_6)$-alkyl, $N((C_1-C_6)$-alkyl$)_2$, $NHCO(C_1-C_6)$-alkyl, phenyl, or $O-(CH_2)_n$-phenyl, wherein n=0-6, and wherein the phenyl ring is unsubstituted or substituted one, two, or three times, each substituent chosen independently from: F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SO_2-CH_3$, COOH, $COO-(C_1-C_6)$-alkyl, and $CONH_2$;

(LAG) is an amino acid residue, or an oligopeptide residue comprising 2 to 9 amino acids;

and wherein at least one of the radicals R1 or R3 must have the meaning:

$(C_1-C_{30})$-alkylene-(LAG), wherein at least one carbon atom of the alkylene radical is replaced by:

aryl or heteroaryl radicals, which are unsubstituted or substituted one, two, or three times by R7, or by $(C_3-C_{10})$-cycloalkyl or heterocycloalkyl radicals, which are unsubstituted or substituted one, two, or three times by R7, or $-S(O)_m-$ (where m=0-2), $-O-$, $-(C=O)-$, $-N(CH_3)-$, $-N(phenyl)-$, $-N(CO-(CH_2)_{1-10}-COOH)-$ or $-NH-$.

3. A compound as claimed in claim 1, wherein

R2, R4, R5, and R6, independently of one another, are chosen from:

H, F, Cl, Br, I, $CF_3$, $NO_2$, $N_3$, CN, COOH, $COO(C_1-C_6)$-alkyl, $CONH_2$, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, or $O-(C_1-C_6)$-alkyl, wherein the alkyl radical is unsubstituted or at least one hydrogen in the alkyl radical is replaced by fluorine; or $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-phenyl, $SO-(C_1-C_6)$-alkyl, $SO-(CH_2)_n$-phenyl, $SO_2-(C_1-C_6)$-alkyl, or $SO_2-(CH_2)_n$-phenyl, wherein n=0-6, and wherein the phenyl radical is unsubstituted or substituted one or two times, each substituent chosen independently from: F, Cl, Br, OH, $CF_3$, $NO_2$, CN, $OCF_3$, $O-(C_1-C_6)$-alkyl, $(C_1-C_6)$-alkyl, and $NH_2$; or $NH_2$, $NH-(C_1-C_6)$-alkyl, $N((C_1-C_6)$-alkyl$)_2$, $NHCO(C_1-C_6)$-alkyl, phenyl, or $O-(CH_2)_n$-phenyl, wherein n=0-6, and wherein the phenyl ring is unsubstituted or substituted one, two, or three times, each substituent chosen independently from: F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SO_2-CH_3$, COOH, $COO-(C_1-C_6)$-alkyl, and $CONH_2$;

R1 and R3, independently of one another, are:

$-(CH_2)_{0-1}-NH-(C=O)_{0-1}-(C_0-C_{25})$-alkylene-$(C=O)_{0-1}-N(R13)_{0-1}$-(LAG) or $-(CH_2)_{0-1}-(C=O)_{0-1}-NH-(C_0-C_{25})$-alkylene-$(C=O)_{0-1}-N(R13)_{0-1}$-(LAG);

wherein at least one carbon atom of the alkylene radical is replaced by:

aryl or heteroaryl radicals, which are unsubstituted or substituted one, two, or three times by R7, or by $(C_3-C_{10})$-cycloalkyl or heterocycloalkyl radicals, which are unsubstituted or substituted one, two, or three times by R7 and wherein at least one or more carbon atom of the alkylene radical is optionally replaced by oxygen atoms; or H, F, Cl, Br, I, $CF_3$, $NO_2$, $N_3$, CN, COOH, $COO(C_1-C_6)$-alkyl, $CONH_2$, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, or $O-(C_1-C_6)$-alkyl, wherein the alkyl radical is unsubstituted or at least one hydrogen in the alkyl radical is replaced by fluorine; or $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-phenyl, $SO-(C_1-C_6)$-alkyl, $SO-(CH_2)_n$-phenyl, $SO_2-(C_1-C_6)$-alkyl, or $SO_2-(CH_2)_n$-phenyl, wherein n=0-6, and wherein the phenyl radical is unsubstituted or substituted one or two times, each substituent chosen independently from: F, Cl, Br, OH, $CF_3$, $NO_2$, CN, $OCF_3$, $O-(C_1-C_6)$-alkyl, $(C_1-C_6)$-alkyl, and $NH_2$; or $NH_2$, $NH-(C_1-C_6)$-alkyl, $N((C_1-C_6)$-alkyl$)_2$, $NHCO(C_1-C_6)$-alkyl, phenyl, or $O-(CH_2)_n$-phenyl, wherein n=0-6, and wherein the phenyl ring is unsubstituted or substituted one, two, or three times, each substituent chosen independently from: F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, COOH, COO—$(C_1-C_6)$-alkyl, and $CONH_2$;

R7 represents F, Cl, Br, I, $CF_3$, $NO_2$, $N_3$, CN, COOH, COO$(C_1-C_6)$-alkyl, $CONH_2$, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, or O—$(C_1-C_6)$-alkyl, wherein the alkyl radical is unsubstituted or at least one hydrogen in the alkyl radical is replaced by fluorine; or $PO_3H_2$, $SO_3H$, $SO_2$—$NH_2$, $SO_2NH(C_1-C_6)$-alkyl, $SO_2N[(C_1-C_6)$-alkyl$]_2$, S—$(C_1-C_6)$-alkyl, S—$(CH_2)_n$-phenyl, SO—$(C_1-C_6)$-alkyl, SO—$(CH_2)_n$-phenyl, $SO_2$-$(C_1-C_6)$-alkyl, or $SO_2$—$(CH_2)_n$-phenyl, wherein n=0-6, and wherein the phenyl radical is unsubstituted or substituted one or two times, each substituent chosen independently from: F, Cl, Br, OH, $CF_3$, $NO_2$, CN, $OCF_3$, O—$(C_1-C_6)$-alkyl, $(C_1-C_6)$-alkyl, and $NH_2$; or $C(NH)(NH_2)$, $NH_2$, NH—$(C_1-C_6)$-alkyl, $N((C_1-C_6)$-alkyl$)_2$, $NHCO(C_1-C_6)$-alkyl, phenyl, or O—$(CH_2)_n$-phenyl, wherein n=0-6, and wherein the phenyl ring is unsubstituted or substituted one, two, or three times, each substituent chosen independently from: F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, COOH, COO—$(C_1-C_6)$-alkyl, and $CONH_2$;

(LAG) is an amino acid residue, or an oligopeptide residue comprising 2 to 9 amino acids;

wherein q=1-5;

R13 represents H or $CH_3$;

and wherein at least one of the radicals R1 or R3 must have the meaning:

—$(CH_2)_{0-1}$—NH—$(C=O)_{0-1}$—$(C_0-C_{25})$-alkylene-$(C=O)_{0-1}$—$N(R13)_{0-1}$-(LAG) or —$(CH_2)_{0-1}$—$(C=O)_{0-1}$—NH—$(C_0-C_{25})$-alkylene-$(C=O)_{0-1}$—$N(R13)_{0-1}$-(LAG), wherein at least one carbon atom of the alkylene radical is replaced by:

aryl or heteroaryl radicals, which are unsubstituted or substituted one, two, or three times by R7, or $(C_3-C_{10})$-cycloalkyl or heterocycloalkyl radicals, which are unsubstituted or substituted one, two, or three times by R7, or —$S(O)_m$—(where m=0-2), —O—, —(C=O)—, —$N(CH_3)$—, —N(phenyl)- or —NH—.

4. A compound as claimed in claim 1, wherein LAG is an amino acid residue.

5. A pharmaceutical composition, comprising an effective amount of at least one compound as claimed in claim 1.

6. A pharmaceutical composition, comprising an effective amount of at least one compound as claimed in claim 1 and at least one additional active compound.

7. The pharmaceutical composition of claim 6, wherein the at least one additional active compound is chosen from compounds that normalize lipid metabolism.

8. The pharmaceutical composition of claim 6, wherein the at least one additional active compound is chosen from antidiabetics, hypoglycemically active compounds, HMG-CoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbers, LDL receptor inducers, ACAT inhibitors, antioxidants, lipoprotein lipase inhibitors, ATP citrate lyase inhibitors, squalene synthetase inhibitors, lipoprotein(a) antagonists, lipase inhibitors, insulins, sulfonylureas, biguanides, nateglinide, repaglinide, mitiglinide, thiazolidinediones, α-glucosidase inhibitors, active compounds which act on the ATP-dependent potassium channel of the beta cells, CART agonists, NPY agonists, MC4 agonists, orexin agonists, TNF-alpha agonists, TNF-beta agonists, TNF-gamma agonists, TNF-delta agonists, TNF-epsilon agonists, CRF agonists, CRF BP antagonists, urorcortin agonists, β3 agonists, MSH (melanocyte-stimulating hormone) agonists, CCK agonists, serotonin-reuptake inhibitors, mixed serotonin and noradrenergic compounds, 5HT agonists, bombesin agonists, galanin antagonists, growth hormones, growth hormone-releasing compounds, agonists, decoupling protein 2 or 3 modulators, leptin agonists, DA agonists, lipase/amylase inhibitors, PPAR modulators, RXR modulators or TR-β-agonists, and amphetamines.

9. A method for treating a patient afflicted with impaired lipid metabolism, comprising administering to a patient in need thereof an effective amount of at least one compound as claimed in claim 1.

10. A process for preparing a pharmaceutical composition comprising at least one compound as claimed in claim 1, comprising mixing the at least one compound with a pharmaceutically acceptable carrier and bringing this mixture into a form suitable for administration.

11. A method for treating hyperlipidemia, comprising administering to a patient in need thereof an effective amount of at least one compound as claimed in claim 1.

12. A method for lowering the serum cholesterol concentration of a patient, comprising administering to a patient in need thereof an effective amount of at least one compound as claimed in claim 1.

13. A method for treating arteriosclerotic manifestations, comprising administering to a patient in need thereof an effective amount of at least one compound as claimed in claim 1.

14. A method for treating a patient afflicted with insulin resistance, comprising administering to a patient in need thereof an effective amount of at least one compound as claimed in claim 1.

15. The pharmaceutical composition of claim 8, wherein the at least one additional active compound is chosen from bromocriptine and 4,7,10,13,16,19-docosahexaenoic acid dopamine conjugate.

\* \* \* \* \*

UNITED STATES PATENT AND TRADEMARK OFFICE
CERTIFICATE OF CORRECTION

PATENT NO. : 7,407,938 B2  Page 1 of 1
APPLICATION NO. : 11/544746
DATED : August 5, 2008
INVENTOR(S) : Gerhard Jaehne et al.

It is certified that error appears in the above-identified patent and that said Letters Patent is hereby corrected as shown below:

In claim 2, column 77, line 41, "$SO_2N[(C_1-C_6)\text{-alkyl}]_2S\text{-}(C_1C_6)\text{-alkyl}$," should read --$SO_2N[(C_1-C_6)\text{-alkyl}]_2, S\text{-}(C_1-C_6)\text{-alkyl}$,--.

In claim 2, column 77, line 42, "$SO\text{-}(CH_2)n\text{-phenyl}$," should read --$SO\text{-}(CH_2)_n\text{-phenyl}$,--.

In claim 8, column 80, lines 11-12, "nateglitinide," should read --nateglinide,--.

In claim 8, column 80, line 18, "urorcortin" should read --urocortin--.

In claim 8, column 80, line 23, "compounds, agonists, decoupling" should read --compounds, decoupling--.

In claim 8, column 80, line 25, "modulators or TR-β-agonists," should read --modulators, TR-β-agonists,--.

Signed and Sealed this

Tenth Day of February, 2009

JOHN DOLL
*Acting Director of the United States Patent and Trademark Office*